United States Patent
Blattman et al.

(10) Patent No.: US 9,944,923 B2
(45) Date of Patent: Apr. 17, 2018

(54) METHODS FOR OBTAINING INFORMATION FROM SINGLE CELLS WITHIN POPULATIONS USING DNA ORIGAMI NANOSTRUCTURES WITHOUT THE NEED FOR SINGLE CELL SORTING

(71) Applicants: Joseph Blattman, Scottsdale, AZ (US); Hao Yan, Chandler, AZ (US); Louis Schoettle, Tempe, AZ (US); Xixi Wei, Mesa, AZ (US)

(72) Inventors: Joseph Blattman, Scottsdale, AZ (US); Hao Yan, Chandler, AZ (US); Louis Schoettle, Tempe, AZ (US); Xixi Wei, Mesa, AZ (US)

(73) Assignee: Arizona Board of Regents on Behalf of Arizona State University, Scottsdale, AZ (US)

( * ) Notice: Subject to any disclaimer, the term of this patent is extended or adjusted under 35 U.S.C. 154(b) by 87 days.

(21) Appl. No.: 14/897,177

(22) PCT Filed: Jun. 9, 2014

(86) PCT No.: PCT/US2014/041581
§ 371 (c)(1),
(2) Date: Dec. 9, 2015

(87) PCT Pub. No.: WO2014/200933
PCT Pub. Date: Dec. 18, 2014

(65) Prior Publication Data
US 2016/0122752 A1    May 5, 2016

Related U.S. Application Data

(60) Provisional application No. 61/834,270, filed on Jun. 12, 2013.

(51) Int. Cl.
*C12Q 1/68* (2006.01)
*C12N 15/10* (2006.01)
*B82Y 5/00* (2011.01)
*B82Y 15/00* (2011.01)

(52) U.S. Cl.
CPC ....... *C12N 15/1062* (2013.01); *C12Q 1/6806* (2013.01); *C12Q 1/6816* (2013.01); *C12Q 1/6881* (2013.01); *B82Y 5/00* (2013.01); *B82Y 15/00* (2013.01); *C12Q 2600/16* (2013.01)

(58) Field of Classification Search
None
See application file for complete search history.

(56) References Cited

U.S. PATENT DOCUMENTS

| | | |
|---|---|---|
| 2010/0047924 A1 | 2/2010 | Webster et al. |
| 2010/0113300 A1 | 5/2010 | Jakobsen et al. |
| 2012/0251583 A1 | 10/2012 | Rothemund |

FOREIGN PATENT DOCUMENTS

| | | |
|---|---|---|
| WO | 2006124089 A1 | 11/2006 |
| WO | 2012058638 A2 | 5/2012 |
| WO | 2013119676 | 8/2013 |
| WO | 2013184754 A1 | 12/2013 |
| WO | WO2013188872 A1 | 12/2013 |

OTHER PUBLICATIONS

Doll, Tais et al., Nanoscale Assemblies and Their Biomedical Applications. Journal of the Royal Society Interface. vol. 10. Jan. 9, 2013; abstract; DOI: 10.1098/rsif.2012.0740.
Schuller, VJ et al. Cellular Immunostimulation by CpG-Sequence-Coated DNA Origami Structuers, ACS Nano. 2011, vol. 5. No. 12, pp. 9696-9702, DOI: 10.1021/nn203161y.

*Primary Examiner* — Celine Qian
(74) *Attorney, Agent, or Firm* — Gavin J. Milczarek-Desai; Quarles & Brady LLP

(57) ABSTRACT

Methods for construction of DNA origami nanostructures, as well as for binding, isolation, linking, and deep sequencing information, such as both of TCR alpha and beta CDR3 mRNA, from individual cells within a mixed population of cells without the need for single cell sorting.

7 Claims, 8 Drawing Sheets

METHODS FOR OBTAINING INFORMATION FROM SINGLE CELLS WITHIN POPULATIONS USING DNA ORIGAMI NANOSTRUCTURES WITHOUT THE NEED FOR SINGLE CELL SORTING

CROSS-REFERENCE

This application is a 371 application of PCT/US2014/041581 filed Jun. 9, 2014, which claims priority to U.S. provisional patent application 61/834,270 filed on Jun. 12, 2013, which are incorporated by reference herein in their entirety.

FIELD OF INVENTION

This application relates to methods for obtaining genetic information from individual cells within mixed cell populations without the need for single cell sorting. In some embodiments, methods are disclosed for construction of DNA origami nanostructures, for binding, isolation, linking, and deep sequencing of both TCR alpha and beta CDR3 mRNA from individual cells within a mixed population of cells.

BACKGROUND OF INVENTION

One cardinal property of the adaptive immune system is diversity: the immune system must be able to recognize and respond to virtually any invading microorganism. In order to generate such diversity, developing B and T cells rearrange a defined set of variable (V), diversity (D), and joining (J) gene segments, with N-nucleotide addition and subtraction at the joints of these gene segments, resulting in a semi-random CDR3 repertoire of immune receptors. Further diversity is generated by pairing of rearranged alpha and beta (for the T cell receptor (TCR)) or heavy and light chain (for the B cell receptor (BCR)).

Current technologies allow for analysis of CDR3 diversity within either the alpha or beta TCR (or heavy and light chain BCR), but no current methods exist for obtaining both CDR3 from individual cells from large polyclonal populations: single cell sequencing remains too expensive while molecular strategies for obtaining linked CDR3 information from single cells have not been adequately developed.

SUMMARY OF THE INVENTION

In certain embodiments, a methodology, including construction of DNA origami nanostructures, for binding, isolation, linking, and deep sequencing of both TCR alpha and beta CDR3 mRNA from individual cells within a mixed population of cells is described. This represents a quantum advance in immunology, as no known methods are available for obtaining linked CDR3 information from individuals cells from large mixed populations of cells; current approaches are only able to obtain CDR3 sequence information on either the TCR alpha or TCR beta: such strategies employ lysis of mixed populations of cells resulting in "scrambling" of genomic DNA and mRNA for each TCR or BCR chain, precluding paired analysis.

DNA origami is the nanoscale folding of DNA to create arbitrary two and three-dimensional shapes at the nanoscale. The specificity of the interactions between complementary base pairs make DNA a useful construction material, through design of its base sequences.

Exemplary DNA origami nanostructures are composed of ssDNA (M13 phage) refolded with complementary ssDNA "staple" sequences into computer design-aided predetermined shapes with selected staples extended with complementary sequences to TCR alpha and beta constant region mRNA. Methods for high efficiency transfection of primary T cells with the developed structures, isolation of DNA origami from transfected cells with specifically bound TCR mRNA, as well as a molecular approach for linking the CDR3 from the TCR alpha and beta mRNA into a single cDNA molecule for use in multiplex CDR3 paired end sequencing using existing technologies also are disclosed.

DETAILED DESCRIPTION OF THE PREFERRED EMBODIMENTS

Figure 1:
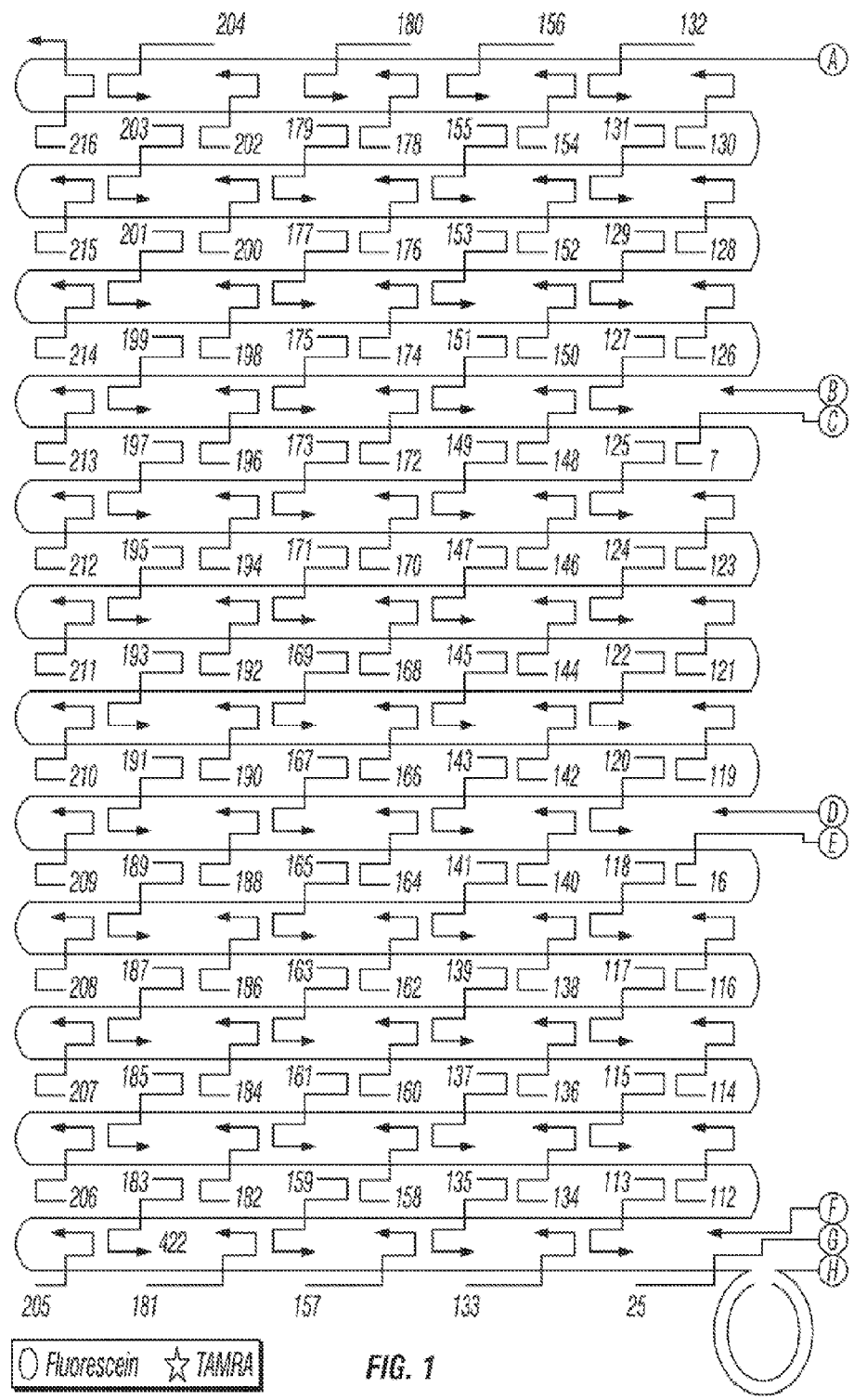
FIG. 1 is a DNA origami scaffold-staple layout for single layer DNA origami objects using square lattice packing including fluorescein and TAMRA fret signals.
Figure 1:
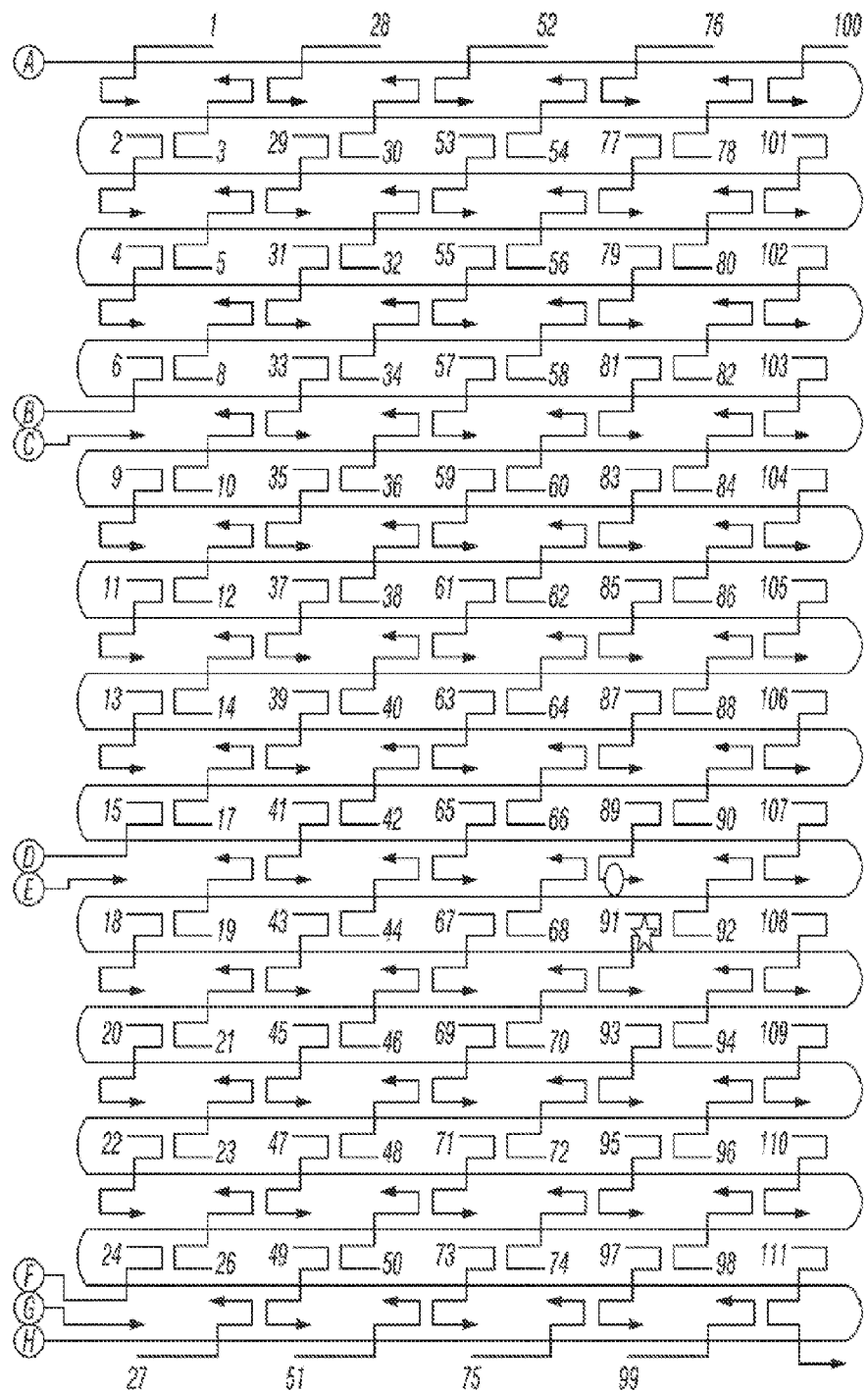

Embodiments described herein relate to methods for high-efficiency transfection and use of DNA origami nanostructures that are able to bind TCR alpha and beta mRNA within transfected cells, strategies for isolation of DNA origami with bound TCR mRNA, and a molecular approach for linking both CDR3 into a single cDNA molecule for use in paired-end deep sequencing. Thus, we have developed a novel strategy for obtaining linked TCR CDR3 sequence information from single cells, without the need for sorting individual cells, which can be used to analyze TCR repertoires including diversity in the pre-immune repertoire as well as subpopulations of cells of interest.

Current approaches to obtaining linked information on CDR3 sequence from individual cells include single cell sorting followed by PCR and conventional sequencing, lysis of cells in oil emulsion droplets and deep sequencing, and nucleic acid bridges. Single cell sorting remains too costly for analysis of large cell populations; each cell/reaction currently costs $1-$2 making analysis of T cell repertoires from even an individual mouse (~$10^7$ T cells) or human (~$10^{12}$ T cells) unfeasible. Lysis of individual cells in oil emulsion droplets currently is only able to yield analysis of a maximum of $10^5$ T cells from any given individual (or a maximum of 1% of the total TCR repertoire). Transfection of nucleic acid bridges into cells results in hybrid structures that are efficiently cleaved by nucleases within transfected cells and destruction of the template, precluding analysis.

We have developed DNA origami nanostructures that are able to bind and protect TCR mRNA within individual transfected T cells. A hurdle to such approaches is transfection efficiency: typically, primary T cell populations exhibit low transfection efficiency (between 10-15%). DNA origami nanostructures have inherently high transfection efficiency properties resulting in >80% transfection efficiency after simple electroporation. Additionally, labeling the origami with a biotin tag and following cell lysis with streptavidin column purification allows the DNA origami nanostructures with bound cellular mRNA to be re-isolated from transfected cells with high efficiency and purity for use in subsequent molecular reactions.

A final hurdle to obtaining linked information on TCR CDR3 sequences from individual cells is that isolated mRNA species, bound to individual DNA origami nanostructures from individual cells, need to become linked into a single cDNA molecule for multiplex PCR, creating an amplicon suitable for paired-end deep sequencing of the two CDR3 regions. We have developed a molecular strategy, using a multi primer system with a reverse transcription reaction that lacks substantial levels of exonuclease activity (so as not to displace the downstream primer) and commercially available T4 ligase to link the upstream and downstream products, resulting in a single cDNA molecule with the TCRα CDR3 at one end and the TCRβ CDR3 at the other. This can then be used with existing TCR multiplex V gene primers and a single Cβ primer to produce linked information on both CDR3 regions in a single ~400 bp DNA molecule for large populations of T cells which can then be used as input for illumina paired-end high throughput sequencing.

Currently, analysis of one TCR CDR3 is used as a diagnostic for disease (the immune response to an infection or tumor is diagnostic for the type of infection or tumor). In addition, analysis of CDR3 sequences has become a staple in both research applications to understand the immune system as well as in clinical applications for assessment of immune competency after immune reconstitution and during aging.

The methods disclosed herein are very adaptable. Essentially, the basic technology used to create the DNA origami nanostructures could be modified by changing the extended complementary staple sequences to allow for hybridization to any two mRNA species of interest for which it is important to understand the sequence of mRNA from individual cells within a mixed population of cells. For example, changing the identity of the probes to match the TCR gamma and delta constant regions, or to match IgH and Igl constant regions of B cell receptors, or to constant regions of immune receptors from other species (i.e. human), or to any two genes of interest.

Thus, while the following examples of the application of the methods herein are given, they are for illustration only and not intended to limit the claims.

DNA Origami Design: The design of the internal DNA origami scaffold-staple layout for single layer DNA origami objects using square lattice packing was accomplished with the software packages Tiamat [base structure published by Rothemund, P. W. K. Folding DNA to create nanoscale shapes and patterns. Nature 440, 297-302 (2006)] (FIG. 1). A long circular single-stranded DNA derived from the bacteriophage M13mp18 genome (Table 1 below; purchased from Affymetrix) is folded into a three-dimensional shape using 216 shorter ssDNA oligomer strands (sequences in Table 2 below; purchased from IDT) that direct folding of the longer M13mp18 ssDNA.

Figure 2:
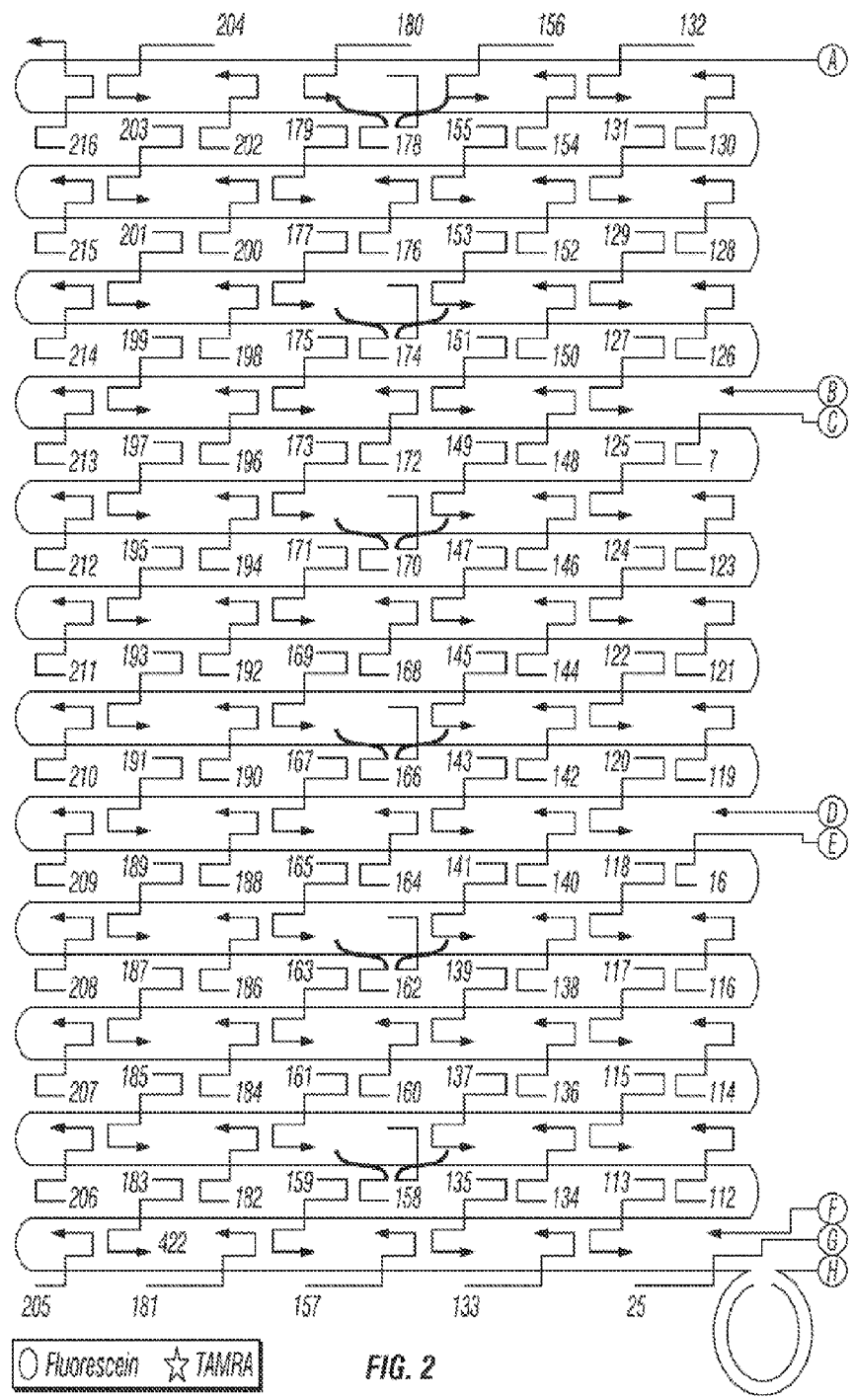
FIG. 2: The sequence of the short oligomer strands are generated using Tiamat software and are defined by the sequence of the scaffold and can be extended to include a single-stranded "probe" sequences that extend from the DNA Origami structure. These sequences are complementary to the conserved regions of the TCR $\alpha$ or $\beta$ mRNA coding sequences (pink and blue respectively, or light and dark when reproduced in black and white), which have been estimated to maintain an "open" secondary structure as established by estimated RNA folding software. The location of the biotin tags on the origami is displayed in black.
Figure 2:
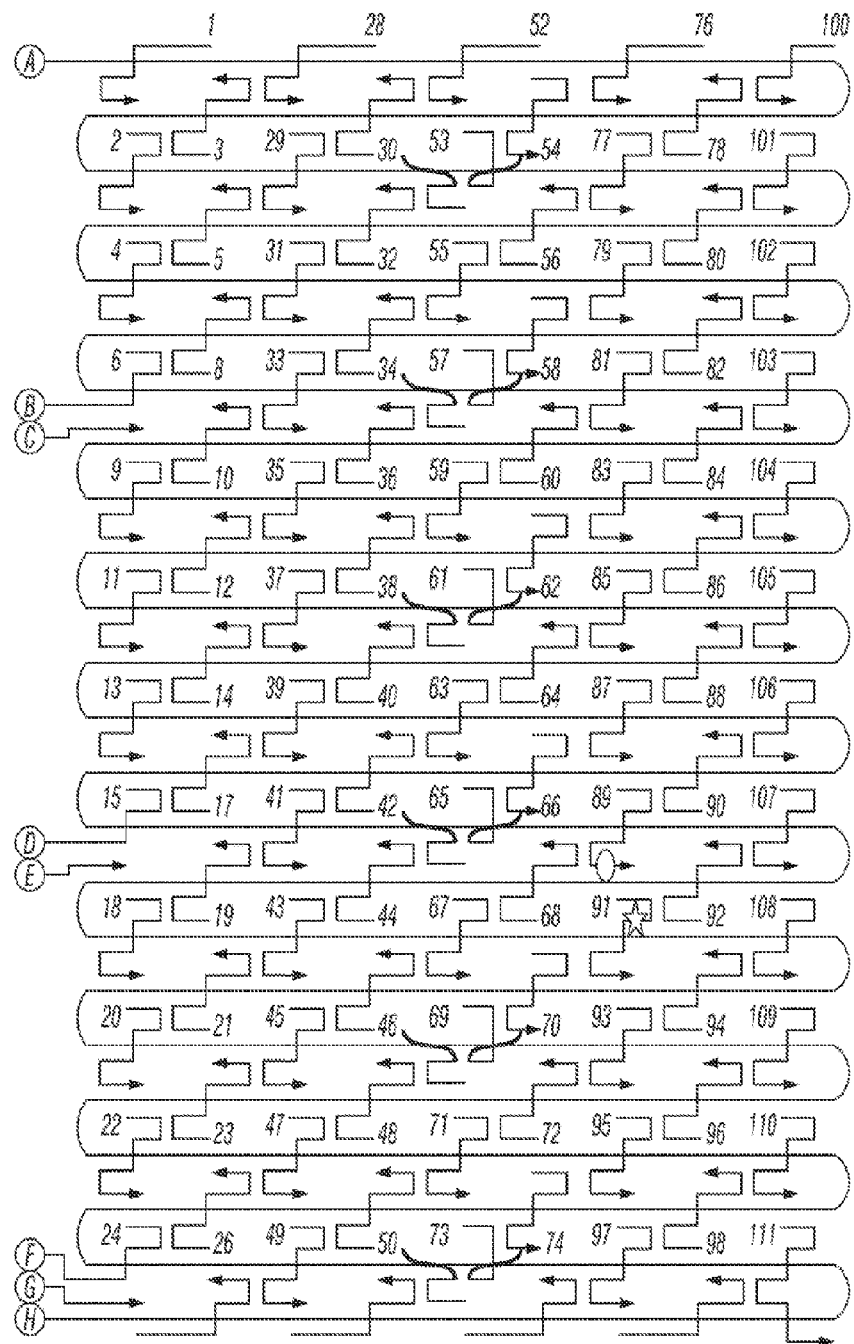
Figure 3:
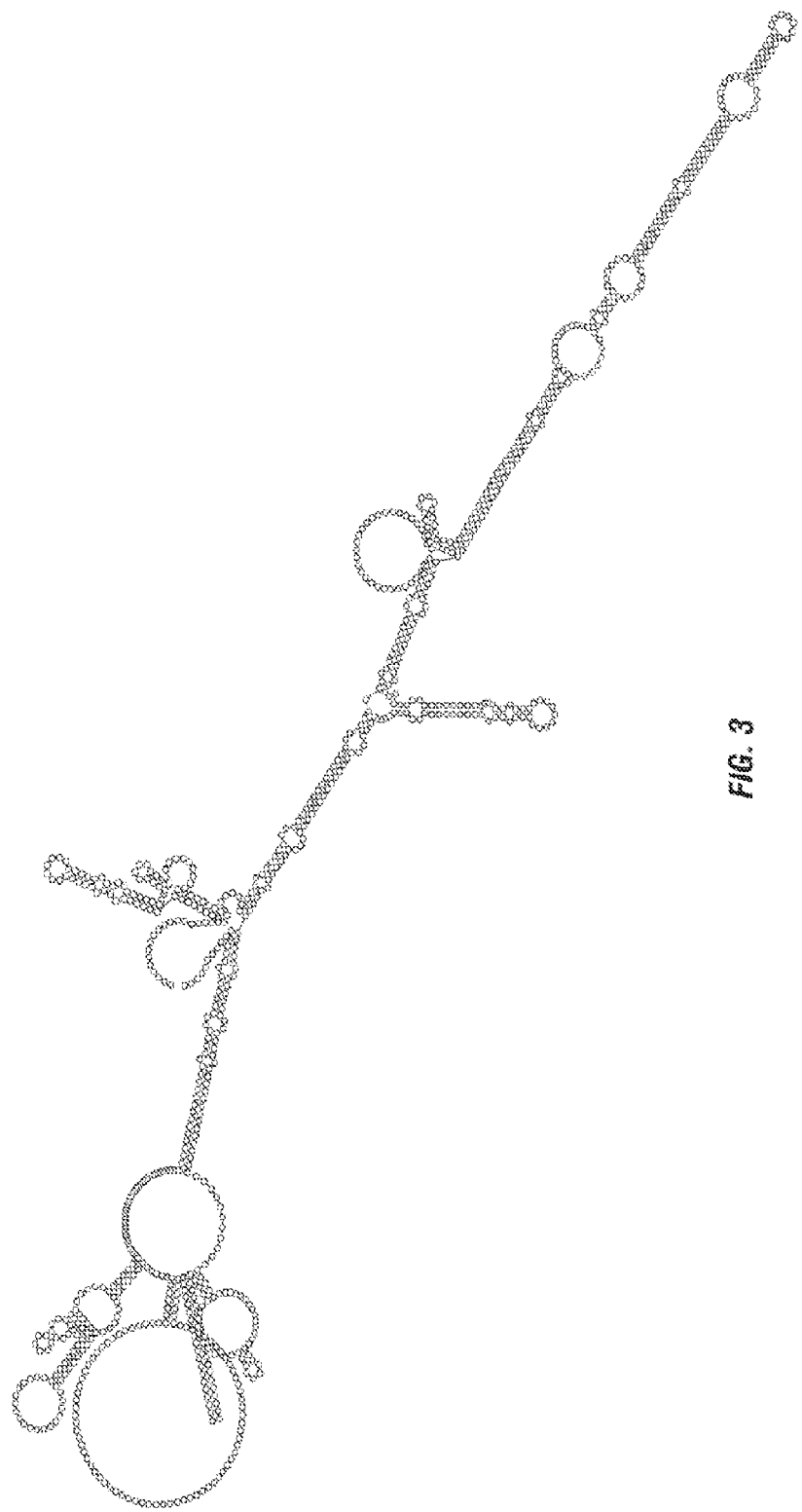
FIG. 3: Estimated "open" secondary structure areas of TCR $\beta$ mRNA as established by predicting RNA folding software. The loops are areas designated for origami probe site attachment.

The sequences of the short oligomer strands are generated using Tiamat software and are defined by the sequence of the scaffold. However, they can be extended to include a single-stranded "probe" sequence that extends from the DNA Origami structure (FIG. 2; sequences in Table 3 below). These sequences are complementary to the conserved regions of the TCR α or β mRNA coding sequences which have been estimated to maintain an "open" secondary structure as established by estimated RNA folding software (FIG. 3). Site-directed attachment of fluorescent dyes TAMRA and FITC to staples 89 and 91 respectively can be included to facilitate detection of transfected cells and subsequent isolation of DNA origami nanostructures with bound TCR mRNA (FIGS. 1 and 2; Table 2). Biotinylation of staples 77, 78, 79 and 80 allows for monomeric avidin resin purification of DNA nanostructures after transfection and cell lysis (FIG. 2; Table 2).

DNA Origami Refolding: The scaffold-staple layout specifies a structural solution for the mixture of scaffold DNA and staple molecules that minimizes energy through Watson-Crick base-pairing. Single-stranded M13mp18 bacteriophage genome (7249 nt) is purchased from the commercial vendor Affymetrix. All oligonucleotide staples are synthesized and procured from the commercial vendor IDT. Alpha and beta staple-probe oligonucleotides are purified and isolated by 10% denaturing-PAGE in 1×TBE with 525 ul 10% APS and 29.4 ul TEMED and purified with Corning Spin X gel filter centrifuge tubes using a freeze-thaw cycle as follows. The PAGE gel is placed on a transluminator. A razor blade is used to cut out major bands from the denaturing-PAGE gel. Bands are chopped into small pieces and small gel blocks are collected into Corning Spin X tubes. 500 uL elution buffer is then added to cut the gel. Samples are then shaken overnight at RT (the aim is to loose the gel and let the DNA migrate out from the pores of the gel into solution, this process is diffusion limited, thus temperature dependent and takes time). Tubes are then centrifuged 8000 rpm, 6 min to separate gel blocks from eluted DNA. 1000 uL butyl alcohol is then added and the tubes are vortexed for 1 min, centrifuged at 2000 rpm, 1 min. The upper layer of butyl alcohol is removed by pipetting (this step is to extract any organic soluble from the DNA sample i.e. EB and tracking dyes). 1000 uL 70% ethyl alcohol is then added and mixed well. Samples are then incubated at −20 C, 2 hr to precipitate DNA. Samples are then centrifuged at 13000 rpm, 30 min at 4 C to pellet the DNA (DNA is not soluble in 70% ethanol). The ethanol is then discarded. Samples are then dried by vacufuging for 2 hr at 30 C. 50 uL nanopure $H_2O$ is then added, samples are vortexed for 1 min to dissolve purified DNA fragments.

Staple oligonucleotides are then standardized to 30 pmol/ul by measuring light absorbance at 260 nm then mixed in equamolar amounts resulting in a master pool with each staple present at 500 nM. Scaffold M13mp18 ssDNA and staple DNA are mixed at a fixed 5:1 stoichiometric ratio (20 nM scaffold, 100 nM each staple) in pH-stabilizing 1×TAE-MG2+ aqueous buffer, followed by thermal denaturation (80° C.) and annealing (23° C.) for 4 hours.

Figure 4:
FIG. 4: Estimated "open" secondary structure areas of TCR $\alpha$ mRNA as established by predicting RNA folding software. The loops are areas designated for origami probe site attachment.

DNA Origami Analysis: Folded DNA origami species are purified from non-folded products and unused primers by washing with butyl alcohol followed by isopropanol, and elution in 50 uL nanopure water and centrifugation through 100K nominal molecular weight limit (NMWL) Amicon microcolumn filters. Purification typically results in a solution containing 2-5 nM of the target DNA origami nanostructure. DNA origami concentration is measured by A260/A280 absorbance and standardization to 50 nM. Isolated nanostructures are visualized by atomic force microscopy (AFM) to verify proper folding (FIG. 4).

Transfection of DNA origami into T cells: Splenocytes from 4-6 week old C57BL/6 mice are prepared by mechanical disruption and red blood cell lysis (0.83% NH4Cl). CD8 T cells are then purified by magnetic cell sorting (MACS Miltenyi Biotech) and >95% purity of sorted populations confirmed by flow cytometry. Cells are pelleted by centrifugation (1200 rpm, 5 min, 4 C), washed with OPTI-MEM media (Invitrogen), and resuspended in OPTI-MEM media at $5\times10^6$ cells/ml. For electroporation, the ECM 830 Square Wave Electroporation System (Harvard Apparatus BTX, Holliston, Mass., USA) is used with the cuvette safety stand attachment and 2.0 mm gap cuvettes (Harvard Apparatus, BTX) using the following settings: Mode=LV, 300 V, 5 ms, 1 pulse, 1.5 kV/cm desired field strength. Samples consist of 100 uL ($5\times10^6$ cells/ml) cell suspension and 25 uL (50 nM) DNA origami suspension in 1×TAE-$Mg^{2+}$. Immediately after electroporation, cells are transferred to a 96 well plate, cuvettes are rinsed with 100 uL fresh culture RPMI-1640 medium with 10% fetal calf serum which is added to the sample and the plates are incubated at 37 C for 24 h. To assess transfection efficiency, cells are stained with anti-CD8-APC antibody (1:100 dilution, BD Biosciences) and immediately acquired on a LSR Fortessa flow cytometer. The DNA origami contain a fluorescein isothiocyanate (FITC; 488 nm excitation, 518 nm emission) tag, and successfully transfected CD8 T cells can be identified by FACS.

Reisolation and purification of origami with bound mRNA: Transfected cells are pelleted by centrifugation at 1300 rpm for 3 min, the supernatant is decanted and the cells are then lysed with 100 uL 1% NP-40 lysis buffer (Thermo Scientific) for 1 hr on ice. Origami from transfected cells are purified by subjecting transfected cell lysate to streptavidin column filtration (Thermo Scientific Streptavidin Agarose Resin; Sigma Prep Column, 500 uL, 7-20 um pore size). 50 uL resin is added to the Prep column, the column is then centrifuged at 2000 rpm for 10 s to remove the storage buffer. The resin is washed with 500 uL 1×TAE$^{Mg2+}$ and centrifuged at 2000 rpm for 10 s. The column is capped and the cell lysate (containing the biotinylated DNA sample) is then incubated with resin in the column for 30 min at RT, shaking by hand every 10 min. The column is then uncapped and the unbound mRNA and cellular debris is washed away using 500 uL 1×TAE$^{Mg2+}$ and centrifuged at 2000 rpm for 10 s, five times. The column is then recapped before reverse transcription.

Figure 6:
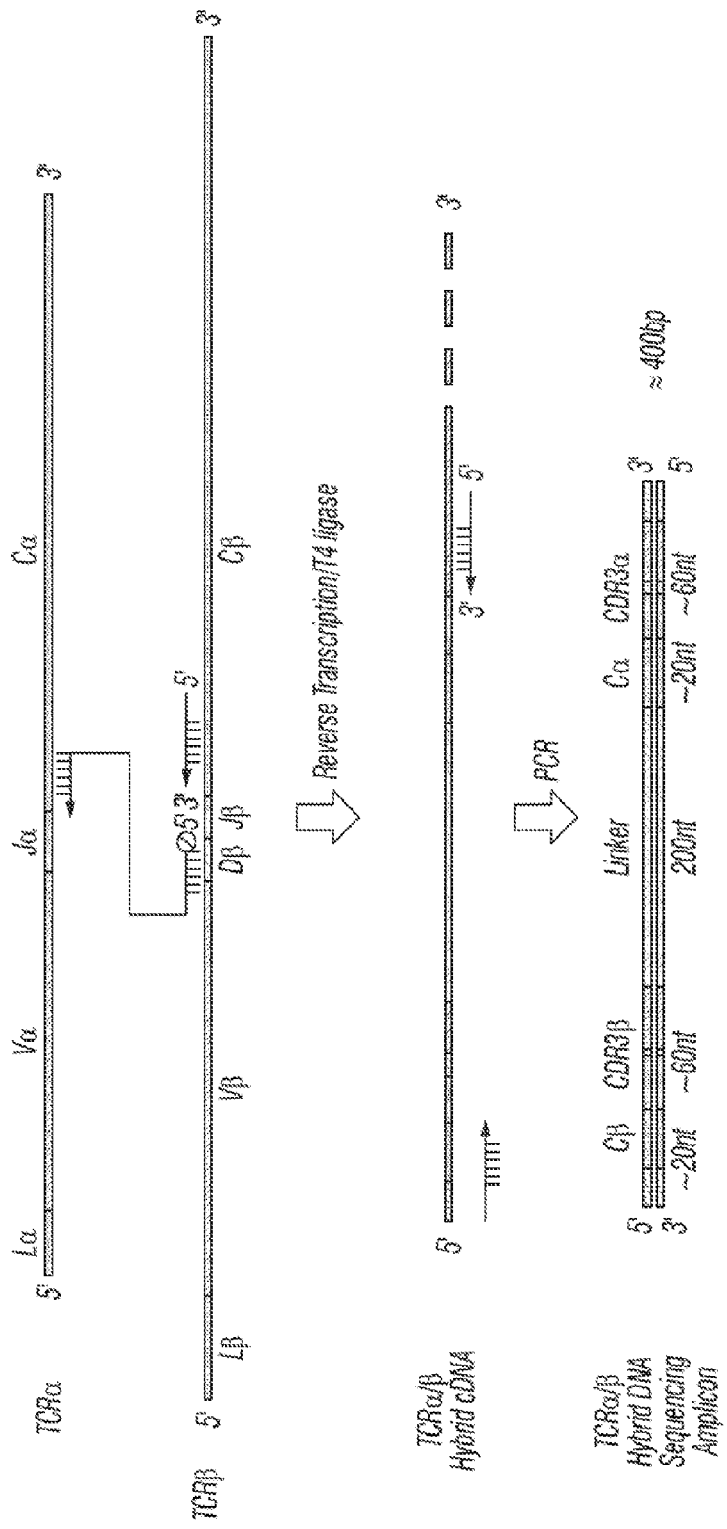
FIG. 6: Reverse transcription, T4 ligation and linkage of origami-bound mRNA to provide input for high throughput sequencing. Our first RT primer attaches to the C$\beta$ region, and utilizing the close proximity of both TCR chains maintained by our origami molecules, we employ a mix of 19 additional 200 nt primers (each specific for a different V$\beta$ gene) which act as a linker from V$\beta$ to C$\alpha$. We then run a reverse transcription reaction with optimized temperature and RNase inhibitor concentration that reduces displacement activity of the RT enzyme. We then follow with an RNA-templated T4 DNA ligation step with optimized temperature, ATP, and enzyme concentrations to produce a TCR$\alpha$/$\beta$ hybrid cDNA molecule which is then amplified by multiplex PCR using a single CP primer and a multiplex V$\alpha$ primer mix (one for each V$\alpha$ gene). The final product is a pool of amplicons around 400 bp in length which serve as input material for high throughput sequencing.

Reverse transcription and linkage of bound mRNA to provide input for high throughput sequencing: After reisolation and purification of origami with bound mRNA, a dual-primer linkage reverse transcription reaction followed by a T4 ligation reaction is performed directly in the purification column to produce cDNA molecules which can then be multiplex-PCR amplified to provide input material for Illumina paired end high throughput sequencing. The first RT primer attaches to an open area of the C13 region, and utilizing the close proximity (and measurable distance) of both TCR chains maintained by our origami molecules, the second set of primers consist of a multiplex pool where each primer is 5'-phosphorylated and acts as a linker from one specific Vβ to Cα (FIG. 6; Table 4). We then run a reverse transcription reaction using the Omniscript RT kit (Qiagen) for 60 min, 37 C, supplemented with 1 uL Ribo-Lock RNase Inhibitor (Thermo Scientific, 40 U/uL), which results in reduced displacement activity of the RT enzyme. We then follow with an RNA-templated T4 DNA ligation step with optimized temperature, duration and ATP concentration to produce a TCRα/β hybrid cDNA molecule (FIG. 6). After ligation, the column is heated to 95 C for 5 min to degrade the origami and dissociate the cDNA from the mRNA. The column is then centrifuged at 2000 rpm for 30 s to elute the cDNA for use in the following multiplex PCR reaction.

Reverse transcription reactions (Omniscript, Qiagen) are performed under conditions that maximize primer annealing and minimize strand displacement activity of the reverse transcriptase enzyme: 15 uL $diH_2O$, 2 uL Omniscript buffer, 2 uL dNTPs (5 mM each), 1 uL RiboLock RNase inhibitor (Thermo Scientific), 1 uL constant alpha primer (100 µM) (Table 4), 3 uL (10-20 uM each) variable beta multiplex linker primer solution (Table 4) and 1 uL reverse transcriptase enzyme is prepared in a PCR tube and added directly to the capped sample purification column and incubated at 37 C for 60 min in a heat block.

RNA-templated T4 DNA ligation is then performed: 7 uL T4 DNA ligase buffer (New England Biolabs) and 2 uL T4 DNA ligase (New England Biolabs) is prepared in a PCR tube and added directly to the capped sample purification columns. The reactions are incubated at RT for 60 min. The caps are removed from the columns and the enzymes are heat inactivated a long with dissociation of origami and mRNA from the ligated cDNA by incubating the columns in a 95 C heat block for 5 min. The ligated cDNA is then eluted from the column by centrifuging at 2000 rpm for 30 s. Collected cDNA is kept on ice until use in following PCR reaction.

Figure 5:
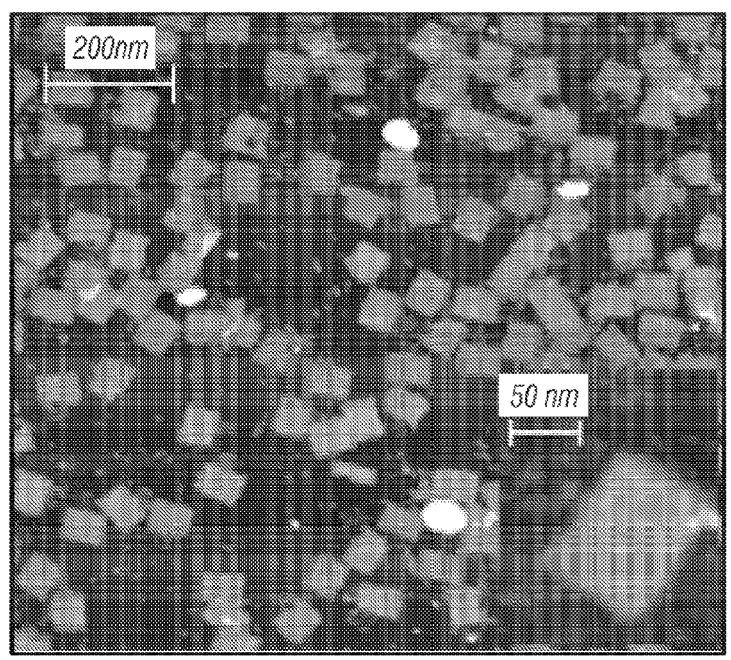
FIG. 5: Isolated nanostructures are visualized by atomic force microscopy (AFM) to verify proper folding.

Multiplex PCR amplification of TCRα/β CDR3 cDNA hybrid molecules: Standard multiplex PCR is performed on the cDNA molecules produced after reverse transcription and T4 ligation reactions utilizing a single 5' phosphorylated Cβ primer (Table 5) and a multiplex 5' phosphorylated Vα primer solution (Table 5). This use of a Taq polymerase results in final DNA molecules (amplicons) consisting of 400-500 bp (FIG. 5) spanning Cα(20 bp)-Jα(variable)-Vα (20 bp)-Linker(200 bp)-Cβ(20 bp)-Jβ(variable)-Dβ(variable)-Vβ(20 bp) (FIG. 5) with 3'A overhangs. Each amplicon is also 5'phosphorylated due to the attached 5'Phos on each primer, allowing for simple ligation of Illumina specific sequencing adaptors per manufacturer's protocol.

TABLE 1

M13mp18 Phage DNA Sequence:

AATGCTACTACTATTAGTAGAATTGATGCCACCTTTTCAGCTCGCGCCCCAAATGA

AAATATAGCTAAACAGGTTATTGACCATTTGCGAAATGTATCTAATGGTCAAACTA

AATCTACTCGTTCGCAGAATTGGGAATCAACTGTTATATGGAATGAAACTTCCAGA

CACCGTACTTTAGTTGCATATTTAAAACATGTTGAGCTACAGCATTATATTCAGCA

ATTAAGCTCTAAGCCATCCGCAAAAATGACCTCTTATCAAAAGGAGCAATTAAAGG

TACTCTCTAATCCTGACCTGTTGGAGTTTGCTTCCGGTCTGGTTCGCTTTGAAGCT

CGAATTAAAACGCGATATTTGAAGTCTTTCGGGCTTCCTCTTAATCTTTTTGATGC

AATCCGCTTTGCTTCTGACTATAATAGTCAGGGTAAAGACCTGATTTTTGATTTAT

GGTCATTCTCGTTTTCTGAACTGTTTAAAGCATTTGAGGGGGATTCAATGAATATT

TATGACGATTCCGCAGTATTGGACGCTATCCAGTCTAAACATTTTACTATTACCCC

CTCTGGCAAAACTTCTTTTGCAAAAGCCTCTCGCTATTTTGGTTTTTATCGTCGTC

TGGTAAACGAGGGTTATGATAGTGTTGCTCTTACTATGCCTCGTAATTCCTTTTGG

CGTTATGTATCTGCATTAGTTGAATGTGGTATTCCTAAATCTCAACTGATGAATCTT

TCTACCTGTAATAATGTTGTTCCGTTAGTTCGTTTTATTAACGTAGATTTTTCTTCC

CAACGTCCTGACTGGTATAATGAGCCAGTTCTTAAAATCGCATAAGGTAATTCACA

ATGATTAAAGTTGAAATTAAACCATCTCAAGCCCAATTTACTACTCGTTCTGGTGTT

TCTCGTCAGGGCAAGCCTTATTCACTGAATGAGCAGCTTTGTTACGTTGATTTGG

GTAATGAATATCCGGTTCTTGTCAAGATTACTCTTGATGAAGGTCAGCCAGCCTAT

GCGCCTGGTCTGTACACCGTTCATCTGTCCTCTTTCAAAGTTGGTCAGTTCGGTT

CCCTTATGATTGACCGTCTGCGCCTCGTTCCGGCTAAGTAACATGGAGCAGGTC

GCGGATTTCGACACAATTTATCAGGCGATGATACAAATCTCCGTTGTACTTTGTTT

CGCGCTTGGTATAATCGCTGGGGGTCAAAGATGAGTGTTTTAGTGTATTCTTTTG

CCTCTTTCGTTTTAGGTTGGTGCCTTCGTAGTGGCATTACGTATTTTACCCGTTTA

ATGGAAACTTCCTCATGAAAAAGTCTTTAGTCCTCAAAGCCTCTGTAGCCGTTGCT

ACCCTCGTTCCGATGCTGTCTTTCGCTGCTGAGGGTGACGATCCCGCAAAAGCG

GCCTTTAACTCCCTGCAAGCCTCAGCGACCGAATATATCGGTTATGCGTGGGCGA

TGGTTGTTGTCATTGTCGGCGCAACTATCGGTATCAAGCTGTTTAAGAAATTCACC

TCGAAAGCAAGCTGATAAACCGATACAATTAAAGGCTCCTTTTGGAGCCTTTTTTT

TGGAGATTTTCAACGTGAAAAAATTATTATTCGCAATTCCTTTAGTTGTTCCTTTCT

ATTCTCACTCCGCTGAAACTGTTGAAAGTTGTTTAGCAAAATCCCATACAGAAAAT

TCATTTACTAACGTCTGGAAAGACGACAAAACTTTAGATCGTTACGCTAACTATGA

GGGCTGTCTGTGGAATGCTACAGGCGTTGTAGTTTGTACTGGTGACGAAACTCAG

TGTTACGGTACATGGGTTCCTATTGGGCTTGCTATCCCTGAAAATGAGGGTGGTG

GCTCTGAGGGTGGCGGTTCTGAGGGTGGCGGTTCTGAGGGTGGCGGTACTAAA

CCTCCTGAGTACGGTGATACACCTATTCCGGGCTATACTTATATCAACCCTCTCG

ACGGCACTTATCCGCCTGGTACTGAGCAAAACCCCGCTAATCCTAATCCTTCTCT

TGAGGAGTCTCAGCCTCTTAATACTTTCATGTTTCAGAATAATAGGTTCCGAAATA

GGCAGGGGGCATTAACTGTTTATACGGGCACTGTTACTCAAGGCACTGACCCCG

TTAAAACTTATTACCAGTACACTCCTGTATCATCAAAAGCCATGTATGACGCTTAC

TABLE 1-continued

M13mp18 Phage DNA Sequence:

TGGAACGGTAAATTCAGAGACTGCGCTTTCCATTCTGGCTTTAATGAGGATTTATT
TGTTTGTGAATATCAAGGCCAATCGTCTGACCTGCCTCAACCTCCTGTCAATGCT
GGCGGCGGCTCTGGTGGTGGTTCTGGTGGCGGCTCTGAGGGTGGTGGCTCTGA
GGGTGGCGGTTCTGAGGGTGGCGGCTCTGAGGGAGGCGGTTCCGGTGGTGGCT
CTGGTTCCGGTGATTTTGATTATGAAAAGATGGCAAACGCTAATAAGGGGGCTAT
GACCGAAAATGCCGATGAAAACGCGCTACAGTCTGACGCTAAAGGCAAACTTGAT
TCTGTCGCTACTGATTACGGTGCTGCTATCGATGGTTTCATTGGTGACGTTTCCG
GCCTTGCTAATGGTAATGGTGCTACTGGTGATTTTGCTGGCTCTAATTCCCAAATG
GCTCAAGTCGGTGACGGTGATAATTCACCTTTAATGAATAATTTCCGTCAATATTT
ACCTTCCCTCCCTCAATCGGTTGAATGTCGCCCTTTTGTCTTTGGCGCTGGTAAA
CCATATGAATTTTCTATTGATTGTGACAAAATAAACTTATTCCGTGGTGTCTTTGCG
TTTCTTTTATATGTTGCCACCTTTATGTATGTATTTTCTACGTTTGCTAACATACTG
CGTAATAAGGAGTCTTAATCATGCCAGTTCTTTTGGGTATTCCGTTATTATTGCGT
TTCCTCGGTTTCCTTCTGGTAACTTTGTTCGGCTATCTGCTTACTTTTCTTAAAAAG
GGCTTCGGTAAGATAGCTATTGCTATTTCATTGTTTCTTGCTCTTATTATTGGGCTT
AACTCAATTCTTGTGGGTTATCTCTCTGATATTAGCGCTCAATTACCCTCTGACTTT
GTTCAGGGTGTTCAGTTAATTCTCCCGTCTAATGCGCTTCCCTGTTTTTATGTTAT
TCTCTCTGTAAAGGCTGCTATTTTCATTTTTGACGTTAAACAAAAAATCGTTTCTTA
TTTGGATTGGGATAAATAATATGGCTGTTTATTTTGTAACTGGCAAATTAGGCTCT
GGAAAGACGCTCGTTAGCGTTGGTAAGATTCAGGATAAAATTGTAGCTGGGTGCA
AAATAGCAACTAATCTTGATTTAAGGCTTCAAAACCTCCCGCAAGTCGGGAGGTT
CGCTAAAACGCCTCGCGTTCTTAGAATACCGGATAAGCCTTCTATATCTGATTTGC
TTGCTATTGGGCGCGGTAATGATTCCTACGATGAAAATAAAAACGGCTTGCTTGTT
CTCGATGAGTGCGGTACTTGGTTTAATACCCGTTCTTGGAATGATAAGGAAAGAC
AGCCGATTATTGATTGGTTTCTACATGCTCGTAAATTAGGATGGGATATTATTTTTC
TTGTTCAGGACTTATCTATTGTTGATAAACAGGCGCGTTCTGCATTAGCTGAACAT
GTTGTTTATTGTCGTCGTCTGGACAGAATTACTTTACCTTTTGTCGGTACTTTATAT
TCTCTTATTACTGGCTCGAAAATGCCTCTGCCTAAATTACATGTTGGCGTTGTTAA
ATATGGCGATTCTCAATTAAGCCCTACTGTTGAGCGTTGGCTTTATACTGGTAAGA
ATTTGTATAACGCATATGATACTAAACAGGCTTTTTCTAGTAATTATGATTCCGGTG
TTTATTCTTATTTAACGCCTTATTTATCACACGGTCGGTATTTCAAACCATTAAATTT
AGGTCAGAAGATGAAATTAACTAAAATATATTTGAAAAAGTTTTCTCGCGTTCTTTG
TCTTGCGATTGGATTTGCATCAGCATTTACATATAGTTATATAACCCAACCTAAGC
CGGAGGTTAAAAAGGTAGTCTCTCAGACCTATGATTTTGATAAATTCACTATTGAC
TCTTCTCAGCGTCTTAATCTAAGCTATCGCTATGTTTTCAAGGATTCTAAGGGAAA
ATTAATTAATAGCGACGATTTACAGAAGCAAGGTTATTCACTCACATATATTGATTT
ATGTACTGTTTCCATTAAAAAAGGTAATTCAAATGAAATTGTTAAATGTAATTAATTT
TGTTTTCTTGATGTTTGTTTCATCATCTTCTTTTGCTCAGGTAATTGAAATGAATAA
TTCGCCTCTGCGCGATTTTGTAACTTGGTATTCAAAGCAATCAGGCGAATCCGTTA

TABLE 1-continued

M13mp18 Phage DNA Sequence:

```
TTGTTTCTCCCGATGTAAAAGGTACTGTTACTGTATATTCATCTGACGTTAAACCT
GAAAATCTACGCAATTTCTTTATTTCTGTTTTACGTGCAAATAATTTTGATATGGTA
GGTTCTAACCCTTCCATTATTCAGAAGTATAATCCAAACAATCAGGATTATATTGAT
GAATTGCCATCATCTGATAATCAGGAATATGATGATAATTCCGCTCCTTCTGGTGG
TTTCTTTGTTCCGCAAAATGATAATGTTACTCAAACTTTTAAAATTAATAACGTTCG
GGCAAAGGATTTAATACGAGTTGTCGAATTGTTTGTAAAGTCTAATACTTCTAAAT
CCTCAAATGTATTATCTATTGACGGCTCTAATCTATTAGTTGTTAGTGCTCCTAAAG
ATATTTTAGATAACCTTCCTCAATTCCTTTCAACTGTTGATTTGCCAACTGACCAGA
TATTGATTGAGGGTTTGATATTTGAGGTTCAGCAAGGTGATGCTTTAGATTTTTCA
TTTGCTGCTGGCTCTCAGCGTGGCACTGTTGCAGGCGGTGTTAATACTGACCGC
CTCACCTCTGTTTTATCTTCTGCTGGTGGTTCGTTCGGTATTTTTAATGGCGATGT
TTTAGGGCTATCAGTTCGCGCATTAAAGACTAATAGCCATTCAAAAATATTGTCTG
TGCCACGTATTCTTACGCTTTCAGGTCAGAAGGGTTCTATCTCTGTTGGCCAGAA
TGTCCCTTTTATTACTGGTCGTGTGACTGGTGAATCTGCCAATGTAAATAATCCAT
TTCAGACGATTGAGCGTCAAAATGTAGGTATTTCCATGAGCGTTTTTCCTGTTGCA
ATGGCTGGCGGTAATATTGTTCTGGATATTACCAGCAAGGCCGATAGTTTGAGTT
CTTCTACTCAGGCAAGTGATGTTATTACTAATCAAAGAAGTATTGCTACAACGGTT
AATTTGCGTGATGGACAGACTCTTTTACTCGGTGGCCTCACTGATTATAAAAACAC
TTCTCAGGATTCTGGCGTACCGTTCCTGTCTAAAATCCCTTTAATCGGCCTCCTGT
TTAGCTCCCGCTCTGATTCTAACGAGGAAAGCACGTTATACGTGCTCGTCAAAGC
AACCATAGTACGCGCCCTGTAGCGGCGCATTAAGCGCGGCGGGTGTGGTGGTTA
CGCGCAGCGTGACCGCTACACTTGCCAGCGCCCTAGCGCCCGCTCCTTTCGCTT
TCTTCCCTTCCTTTCTCGCCACGTTCGCCGGCTTTCCCCGTCAAGCTCTAAATCG
GGGGCTCCCTTTAGGGTTCCGATTTAGTGCTTTACGGCACCTCGACCCCAAAAAA
CTTGATTTGGGTGATGGTTCACGTAGTGGGCCATCGCCCTGATAGACGGTTTTTC
GCCCTTTGACGTTGGAGTCCACGTTCTTTAATAGTGGACTCTTGTTCCAAACTGG
AACAACACTCAACCCTATCTCGGGCTATTCTTTTGATTTATAAGGGATTTTGCCGA
TTTCGGAACCACCATCAAACAGGATTTTCGCCTGCTGGGGCAAACCAGCGTGGA
CCGCTTGCTGCAACTCTCTCAGGGCCAGGCGGTGAAGGGCAATCAGCTGTTGCC
CGTCTCACTGGTGAAAAGAAAAACCACCCTGGCGCCCAATACGCAAACCGCCTC
TCCCCGCGCGTTGGCCGATTCATTAATGCAGCTGGCACGACAGGTTTCCCGACT
GGAAAGCGGGCAGTGAGCGCAACGCAATTAATGTGAGTTAGCTCACTCATTAGG
CACCCCAGGCTTTACACTTTATGCTTCCGGCTCGTATGTTGTGTGGAATTGTGAG
CGGATAACAATTTCACACAGGAAACAGCTATGACCATGATTACGAATTCGAGCTC
GGTACCCGGGGATCCTCTAGAGTCGACCTGCAGGCATGCAAGCTTGGCACTGGC
CGTCGTTTTACAACGTCGTGACTGGGAAAACCCTGGCGTTACCCAACTTAATCGC
CTTGCAGCACATCCCCCTTTCGCCAGCTGGCGTAATAGCGAAGAGGCCCGCACC
GATCGCCCTTCCCAACAGTTGCGCAGCCTGAATGGCGAATGGCGCTTTGCCTGG
TTTCCGGCACCAGAAGCGGTGCCGGAAAGCTGGCTGGAGTGCGATCTTCCTGAG
```

TABLE 1-continued

M13mp18 Phage DNA Sequence:

GCCGATACTGTCGTCGTCCCCTCAAACTGGCAGATGCACGGTTACGATGCGCCC

ATCTACACCAACGTGACCTATCCCATTACGGTCAATCCGCCGTTTGTTCCCACGG

AGAATCCGACGGGTTGTTACTCGCTCACATTTAATGTTGATGAAAGCTGGCTACA

GGAAGGCCAGACGCGAATTATTTTTGATGGCGTTCCTATTGGTTAAAAAATGAGC

TGATTTAACAAAAATTTAATGCGAATTTTAACAAAATATTAACGTTTACAATTTAAAT

ATTTGCTTATACAATCTTCCTGTTTTTGGGGCTTTTCTGATTATCAACCGGGGTAC

ATATGATTGACATGCTAGTTTTACGATTACCGTTCATCGATTCTCTTGTTTGCTCCA

GACTCTCAGGCAATGACCTGATAGCCTTTGTAGATCTCTCAAAAATAGCTACCCTC

TCCGGCATTAATTTATCAGCTAGAACGGTTGAATATCATATTGATGGTGATTTGAC

TGTCTCCGGCCTTTCTCACCCTTTTGAATCTTTACCTACACATTACTCAGGCATTG

CATTTAAAATATATGAGGGTTCTAAAAATTTTTATCCTTGCGTTGAAATAAAGGCTT

CTCCCGCAAAAGTATTACAGGGTCATAATGTTTTTGGTACAACCGATTTAGCTTTA

TGCTCTGAGGCTTTATTGCTTAATTTTGCTAATTCTTTGCCTTGCCTGTATGATTTA

TTGGATGTT (SEQ ID NO. 1)

TABLE 2

Staple sequences of DNA origami:

| Name | Sequence |
|---|---|
| 1 | CAAGCCCAATAGGAAC CCATGTACAAACAGTT (SEQ ID NO.2) |
| 2 | AATGCCCCGTAACAGT GCCCGTATCTCCCTCA (SEQ ID NO. 3) |
| 3 | TGCCTTGACTGCCTAT TTCGGAACAGGGATAG (SEQ ID NO. 4) |
| 4 | GAGCCGCCCCACCACC GGAACCGCGACGGAAA (SEQ ID NO. 5) |
| 5 | AACCAGAGACCCTCAG AACCGCCAGGGGTCAG (SEQ ID NO. 6) |
| 6 | TTATTCATAGGGAAGG TAAATATT CATTCAGT (SEQ ID NO. 7) |
| 7 | CATAACCCGAGGCATA GTAAGAGC TTTTTAAG (SEQ ID NO. 8) |
| 8 | ATTGAGGGTAAAGGTG AATTATCAATCACCGG (SEQ ID NO. 9) |
| 9 | AAAAGTAATATCTTAC CGAAGCCCTTCCAGAG (SEQ ID NO. 10) |
| 10 | GCAATAGCGCAGATAG CCGAACAATTCAACCG (SEQ ID NO. 11) |
| 11 | CCTAATTTACGCTAAC GAGCGTCTAATCAATA (SEQ ID NO. 12) |
| 12 | TCTTACCAGCCAGTTA CAAAATAAATGAAATA (SEQ ID NO. 13) |
| 13 | ATCGGCTGCGAGCATG TAGAAACCTATCATAT (SEQ ID NO. 14) |
| 14 | CTAATTTATCTTTCCT TATCATTCATCCTGAA (SEQ ID NO. 15) |
| 15 | GCGTTATAGAAAAAGC CTGTTTAG AAGGCCGG (SEQ ID NO. 16) |
| 16 | GCTCATTTTCGCATTA AATTTTTG AGCTTAGA (SEQ ID NO. 17) |
| 17 | AATTACTACAAATTCT TACCAGTAATCCCATC (SEQ ID NO. 18) |
| 18 | TTAAGACGTTGAAAAC ATAGCGATAACAGTAC (SEQ ID NO. 19) |
| 19 | TAGAATCCCTGAGAAG AGTCAATAGGAATCAT (SEQ ID NO. 20) |
| 20 | CTTTTACACAGATGAA TATACAGTAAACAATT (SEQ ID NO. 21) |
| 21 | TTTAACGTTCGGGAGA AACAATAATTTTCCCT (SEQ ID NO. 22) |

TABLE 2-continued

Staple sequences of DNA origami:

| Name | Sequence |
|------|----------|
| 22 | CGACAACTAAGTATTA GACTTTACAATACCGA (SEQ ID NO. 23) |
| 23 | GGATTTAGCGTATTAA ATCCTTTGTTTTCAGG (SEQ ID NO. 24) |
| 24 | ACGAACCAAAACATCG CCATTAAA TGGTGGTT (SEQ ID NO. 25) |
| 25 | GAACGTGGCGAGAAAG GAAGGGAA CAAACTAT (SEQ ID NO. 26) |
| 26 | TAGCCCTACCAGCAGA AGATAAAAACATTTGA (SEQ ID NO. 27) |
| 27 | CGGCCTTGCTGGTAAT ATCCAGAACGAACTGA (SEQ ID NO. 28) |
| 28 | CTCAGAGCCACCACCC TCATTTTCCTATTATT (SEQ ID NO. 29) |
| 29 | CTGAAACAGGTAATAA GTTTTAACCCCTCAGA (SEQ ID NO. 30) |
| 30 | AGTGTACTTGAAAGTA TTAAGAGGCCGCCACC (SEQ ID NO. 31) |
| 31 | GCCACCACTCTTTTCA TAATCAAACCGTCACC (SEQ ID NO. 32) |
| 32 | GTTTGCCACCTCAGAG CCGCCACCGATACAGG (SEQ ID NO. 33) |
| 33 | GACTTGAGAGACAAAA GGGCGACAAGTTACCA (SEQ ID NO. 34) |
| 34 | AGCGCCAACCATTTGG GAATTAGATTATTAGC (SEQ ID NO. 35) |
| 35 | GAAGGAAAATAAGAGC AAGAAACAACAGCCAT (SEQ ID NO. 36) |
| 36 | GCCCAATACCGAGGAA ACGCAATAGGTTTACC (SEQ ID NO. 37) |
| 37 | ATTATTTAACCCAGCT ACAATTTTCAAGAACG (SEQ ID NO. 38) |
| 38 | TATTTTGCTCCCAATC CAAATAAGTGAGTTAA (SEQ ID NO. 39) |
| 39 | GGTATTAAGAACAAGA AAAATAATTAAAGCCA (SEQ ID NO. 40) |
| 40 | TAAGTCCTACCAAGTA CCGCACTCTTAGTTGC (SEQ ID NO. 41) |
| 41 | ACGCTCAAAATAAGAA TAAACACCGTGAATTT (SEQ ID NO. 42) |
| 42 | AGGCGTTACAGTAGGG CTTAATTGACAATAGA (SEQ ID NO. 43) |
| 43 | ATCAAAATCGTCGCTA TTAATTAACGGATTCG (SEQ ID NO. 44) |
| 44 | CTGTAAATCATAGGTC TGAGAGACGATAAATA (SEQ ID NO. 45) |
| 45 | CCTGATTGAAAGAAAT TGCGTAGACCCGAACG (SEQ ID NO. 46) |
| 46 | ACAGAAATCTTTGAAT ACCAAGTTCCTTGCTT (SEQ ID NO. 47) |
| 47 | TTATTAATGCCGTCAA TAGATAATCAGAGGTG (SEQ ID NO. 48) |
| 48 | AGATTAGATTTAAAAG TTTGAGTACACGTAAA (SEQ ID NO. 49) |
| 49 | AGGCGGTCATTAGTCT TTAATGCGCAATATTA (SEQ ID NO. 50) |
| 50 | GAATGGCTAGTATTAA CACCGCCTCAACTAAT (SEQ ID NO. 51) |
| 51 | CCGCCAGCCATTGCAA CAGGAAAAATATTTTT (SEQ ID NO. 52) |
| 52 | CCCTCAGAACCGCCAC CCTCAGAACTGAGACT (SEQ ID NO. 53) |
| 53 | CCTCAAGAATACATGG CTTTTGATAGAACCAC (SEQ ID NO. 54) |
| 54 | TAAGCGTCGAAGGATT AGGATTAGTACCGCCA (SEQ ID NO. 55) |
| 55 | CACCAGAGTTCGGTCA TAGCCCCCGCCAGCAA (SEQ ID NO. 56) |
| 56 | TCGGCATTCCGCCGCC AGCATTGACGTTCCAG (SEQ ID NO. 57) |
| 57 | AATCACCAAATAGAAA ATTCATATATAACGGA (SEQ ID NO. 58) |
| 58 | TCACAATCGTAGCACC ATTACCATCGTTTTCA (SEQ ID NO. 59) |
| 59 | ATACCCAAGATAACCC ACAAGAATAAACGATT (SEQ ID NO. 60) |

TABLE 2-continued

Staple sequences of DNA origami:

| Name | Sequence |
|---|---|
| 60 | ATCAGAGAAAGAACTG GCATGATTTTATTTTG (SEQ ID NO. 61) |
| 61 | TTTTGTTTAAGCCTTA AATCAAGAATCGAGAA (SEQ ID NO. 62) |
| 62 | AGGTTTTGAACGTCAA AAATGAAAGCGCTAAT (SEQ ID NO. 63) |
| 63 | CAAGCAAGACGCGCCT GTTTATCAAGAATCGC (SEQ ID NO. 64) |
| 64 | AATGCAGACCGTTTTT ATTTTCATCTTGCGGG (SEQ ID NO. 65) |
| 65 | CATATTTAGAAATACC GACCGTGTTACCTTTT (SEQ ID NO. 66) |
| 66 | AATGGTTTACAACGCC AACATGTAGTTCAGCT (SEQ ID NO. 67) |
| 67 | TAACCTCCATATGTGA GTGAATAAACAAAATC (SEQ ID NO. 68) |
| 68 | AAATCAATGGCTTAGG TTGGGTTACTAAATTT (SEQ ID NO. 69) |
| 69 | GCGCAGAGATATCAAA ATTATTTGACATTATC (SEQ ID NO. 70) |
| 70 | AACCTACCGCGAATTA TTCATTTCCAGTACAT (SEQ ID NO. 71) |
| 71 | ATTTTGCGTCTTTAGG AGCACTAAGCAACAGT (SEQ ID NO. 72) |
| 72 | CTAAAATAGAACAAAG AAACCACCAGGGTTAG (SEQ ID NO. 73) |
| 73 | GCCACGCTATACGTGG CACAGACAACGCTCAT (SEQ ID NO. 74) |
| 74 | GCGTAAGAGAGAGCCA GCAGCAAAAAGGTTAT (SEQ ID NO. 75) |
| 75 | GGAAATACCTACATTT TGACGCTCACCTGAAA (SEQ ID NO. 76) |
| 76 | TATCACCGTACTCAGG AGGTTTAGCGGGGTTT (SEQ ID NO. 77) |
| 77 | TGCTCAGTCAGTCTCT GAATTTACCAGGAGGT (SEQ ID NO. 78) |
| 78 | GGAAAGCGACCAGGCG GATAAGTGAATAGGTG (SEQ ID NO. 79) |
| 79 | TGAGGCAGGCGTCAGA CTGTAGCGTAGCAAGG (SEQ ID NO. 80) |
| 80 | TGCCTTTAGTCAGACG ATTGGCCTGCCAGAAT (SEQ ID NO. 81) |
| 81 | CCGGAAACACACCACG GAATAAGTAAGACTCC (SEQ ID NO. 82) |
| 82 | ACGCAAAGGTCACCAA TGAAACCAATCAAGTT (SEQ ID NO. 83) |
| 83 | TTATTACGGTCAGAGG GTAATTGAATAGCAGC (SEQ ID NO. 84) |
| 84 | TGAACAAACAGTATGT TAGCAAACTAAAAGAA (SEQ ID NO. 85) |
| 85 | CTTTACAGTTAGCGAA CCTCCCGACGTAGGAA (SEQ ID NO. 86) |
| 86 | GAGGCGTTAGAGAATA ACATAAAAGAACACCC (SEQ ID NO. 87) |
| 87 | TCATTACCCGACAATA AACAACATATTTAGGC (SEQ ID NO. 88) |
| 88 | CCAGACGAGCGCCCAA TAGCAAGCAAGAACGC (SEQ ID NO. 89) |
| 89 | AGAGGCATAATTTCAT CTTCTGACTATAACTA (SEQ ID NO. 90) |
| 90 | TTTTAGTTTTTCGAGC CAGTAATAAATTCTGT (SEQ ID NO. 91) |
| 91 | TATGTAAACCTTTTTT AATGGAAAAATTACCT (SEQ ID NO. 92) |
| 92 | TTGAATTATGCTGATG CAAATCCACAAATATA (SEQ ID NO. 93) |
| 93 | GAGCAAAAACTTCTGA ATAATGGAAGAAGGAG (SEQ ID NO. 94) |
| 94 | TGGATTATGAAGATGA TGAAACAAAATTTCAT (SEQ ID NO. 95) |
| 95 | CGGAATTATTGAAAGG AATTGAGGTGAAAAAT (SEQ ID NO. 96) |
| 96 | ATCAACAGTCATCATA TTCCTGATTGATTGTT (SEQ ID NO. 97) |
| 97 | CTAAAGCAAGATAGAA CCCTTCTGAATCGTCT (SEQ ID NO. 98) |

TABLE 2-continued

Staple sequences of DNA origami:

| Name | Sequence |
|---|---|
| 98 | GCCAACAGTCACCTTG CTGAACCTGTTGGCAA (SEQ ID NO. 99) |
| 99 | GAAATGGATTATTTAC ATTGGCAGACATTCTG (SEQ ID NO. 100) |
| 100 | TTTT TATAAGTA TAGCCCGGCCGTCGAG (SEQ ID NO. 101) |
| 101 | AGGGTTGA TTTT ATAAATCC TCATTAAATGATATTC (SEQ ID NO. 102) |
| 102 | ACAAACAA TTTT AATCAGTA GCGACAGATCGATAGC (SEQ ID NO. 103) |
| 103 | AGCACCGT TTTT TAAAGGTG GCAACATAGTAGAAAA (SEQ ID NO. 104) |
| 104 | TACATACA TTTT GACGGGAG AATTAACTACAGGGAA (SEQ ID NO. 105) |
| 105 | GCGCATTA TTTT GCTTATCC GGTATTCTAAATCAGA (SEQ ID NO. 106) |
| 106 | TATAGAAG TTTT CGACAAAA GGTAAAGTAGAGAATA (SEQ ID NO. 107) |
| 107 | TAAAGTAC TTTT CGCGAGAA AACTTTTTATCGCAAG (SEQ ID NO. 108) |
| 108 | ACAAACAA TTTT ATTAATTA CATTTAACACATCAAG (SEQ ID NO. 109) |
| 109 | AAAACAAA TTTT TTCATCAA TATAATCCTATCAGAT (SEQ ID NO. 110) |
| 110 | GATGGCAA TTTT AATCAATA TCTGGTCACAAATATC (SEQ ID NO. 111) |
| 111 | AAACCCTC TTTT ACCAGTAA TAAAAGGGATTCACCA GTCACACG TTTT (SEQ ID NO. 112) |
| 112 | CCGAAATCCGAAAATC CTGTTTGAAGCCGGAA (SEQ ID NO. 113) |
| 113 | CCAGCAGGGGCAAAATCCCTTATAAAGCCGGC (SEQ ID NO. 114) |
| 114 | GCATAAAGTTCCACAC AACATACGAAGCGCCA (SEQ ID NO. 115) |
| 115 | GCTCACAATGTAAAGCCTGGGGTGGGTTTGCC (SEQ ID NO. 116) |
| 116 | TTCGCCATTGCCGGAA ACCAGGCATTAAATCA (SEQ ID NO. 117) |
| 117 | GCTTCTGGTCAGGCTGCGCAACTGTGTTATCC (SEQ ID NO. 118) |
| 118 | GTTAAAATTTTAACCAATAGGAACCCGGCACC (SEQ ID NO. 119) |
| 119 | AGACAGTCATTCAAAA GGGTGAGAAGCTATAT (SEQ ID NO. 120) |
| 120 | AGGTAAAGAAATCACCATCAATATAATATTTT (SEQ ID NO. 121) |
| 121 | TTTCATTTGGTCAATA ACCTGTTTATATCGCG (SEQ ID NO. 122) |
| 122 | TCGCAAATGGGCGCGAGCTGAAATAATGTGT (SEQ ID NO. 123) |
| 123 | TTTTAATTGCCCGAAA GACTTCAAAACACTAT (SEQ ID NO. 124) |
| 124 | AAGAGGAACGAGCTTCAAAGCGAAGATACATT (SEQ ID NO. 125) |
| 125 | GGAATTACTCGTTTACCAGACGACAAAAGATT (SEQ ID NO. 126) |
| 126 | GAATAAGGACGTAACA AAGCTGCTCTAAAACA (SEQ ID NO. 127) |
| 127 | CCAAATCACTTGCCCTGACGAGAACGCCAAAA (SEQ ID NO. 128) |
| 128 | CTCATCTTGAGGCAAA AGAATACAGTGAATTT (SEQ ID NO. 129) |
| 129 | AAACGAAATGACCCCCAGCGATTATTCATTAC (SEQ ID NO. 130) |
| 130 | CTTAAACATCAGCTTG CTTTCGAGCGTAACAC (SEQ ID NO. 131) |
| 131 | TCGGTTTAGCTTGATACCGATAGTCCAACCTA (SEQ ID NO. 132) |
| 132 | TGAGTTTCGTCACCAGTACAAACTTAATTGTA (SEQ ID NO. 133) |
| 133 | CCCCGATTTAGAGCTTGACGGGGAAATCAAAA (SEQ ID NO. 134) |
| 134 | GAATAGCCGCAAGCGGTCCACGCTCCTAATGA (SEQ ID NO. 135) |

TABLE 2-continued

Staple sequences of DNA origami:

| Name | Sequence |
|------|----------|
| 135 | GAGTTGCACGAGATAGGGTTGAGTAAGGGAGC (SEQ ID NO. 136) |
| 136 | GTGAGCTAGTTTCCTGTGTGAAATTTGGGAAG (SEQ ID NO. 137) |
| 137 | TCATAGCTACTCACATTAATTGCGCCCTGAGA (SEQ ID NO. 138) |
| 138 | GGCGATCGCACTCCAGCCAGCTTTGCCATCAA (SEQ ID NO. 139) |
| 139 | GAAGATCGGTGCGGGCCTCTTCGCAATCATGG (SEQ ID NO. 140) |
| 140 | AAATAATTTTAAATTGTAAACGTTGATATTCA (SEQ ID NO. 141) |
| 141 | GCAAATATCGCGTCTGGCCTTCCTGGCCTCAG (SEQ ID NO. 142) |
| 142 | ACCGTTCTAAATGCAATGCCTGAGAGGTGGCA (SEQ ID NO. 143) |
| 143 | TATATTTTAGCTGATAAATTAATGTTGTATAA (SEQ ID NO. 144) |
| 144 | TCAATTCTTTTAGTTTGACCATTACCAGACCG (SEQ ID NO. 145) |
| 145 | CGAGTAGAACTAATAGTAGTAGCAAACCCTCA (SEQ ID NO. 146) |
| 146 | GAAGCAAAAAAGCGGATTGCATCAGATAAAAA (SEQ ID NO. 147) |
| 147 | TCAGAAGCCTCCAACAGGTCAGGATCTGCGAA (SEQ ID NO. 148) |
| 148 | CCAAAATATAATGCAGATACATAAACACCAGA (SEQ ID NO. 149) |
| 149 | CATTCAACGCGAGAGGCTTTTGCATATTATAG (SEQ ID NO. 150) |
| 150 | ACGAGTAGTGACAAGAACCGGATATACCAAGC (SEQ ID NO. 151) |
| 151 | AGTAATCTTAAATTGGGCTTGAGAGAATACCA (SEQ ID NO. 152) |
| 152 | GCGAAACATGCCACTACGAAGGCATGCGCCGA (SEQ ID NO. 153) |
| 153 | ATACGTAAAAGTACAACGGAGATTTCATCAAG (SEQ ID NO. 154) |
| 154 | CAATGACACTCCAAAAGGAGCCTTACAACGCC (SEQ ID NO. 155) |
| 155 | AAAAAAGGACAACCATCGCCCACGCGGGTAAA (SEQ ID NO. 156) |
| 156 | TGTAGCATTCCACAGACAGCCCTCATCTCCAA (SEQ ID NO. 157) |
| 157 | GTAAAGCACTAAATCGGAACCCTAGTTGTTCC (SEQ ID NO. 158) |
| 158 | AGTTTGGAGCCCTTCACCGCCTGGTTGCGCTC (SEQ ID NO. 159) |
| 159 | AGCTGATTACAAGAGTCCACTATTGAGGTGCC (SEQ ID NO. 160) |
| 160 | ACTGCCCGCCGAGCTCGAATTCGTTATTACGC (SEQ ID NO. 161) |
| 161 | CCCGGGTACTTTCCAGTCGGGAAACGGGCAAC (SEQ ID NO. 162) |
| 162 | CAGCTGGCGGACGACGACAGTATCGTAGCCAG (SEQ ID NO. 163) |
| 163 | GTTTGAGGGAAAGGGGGATGTGCTAGAGGATC (SEQ ID NO. 164) |
| 164 | CTTTCATCCCCAAAAACAGGAAGACCGGAGAG (SEQ ID NO. 165) |
| 165 | AGAAAAGCAACATTAAATGTGAGCATCTGCCA (SEQ ID NO. 166) |
| 166 | GGTAGCTAGGATAAAAATTTTTAGTTAACATC (SEQ ID NO. 167) |
| 167 | CAACGCAATTTTTGAGAGATCTACTGATAATC (SEQ ID NO. 168) |
| 168 | CAATAAATACAGTTGATTCCCAATTTAGAGAG (SEQ ID NO. 169) |
| 169 | TCCATATACATACAGGCAAGGCAACTTTATTT (SEQ ID NO. 170) |
| 170 | TACCTTTAAGGTCTTTACCCTGACAAAGAAGT (SEQ ID NO. 171) |
| 171 | CAAAAATCATTGCTCCTTTTGATAAGTTTCAT (SEQ ID NO. 172) |
| 172 | TTTGCCAGATCAGTTGAGATTTAGTGGTTTAA (SEQ ID NO. 173) |

TABLE 2-continued

Staple sequences of DNA origami:

| Name | Sequence |
|---|---|
| 173 | AAAGATTCAGGGGGTAATAGTAAACCATAAAT (SEQ ID NO. 174) |
| 174 | TTTCAACTATAGGCTGGCTGACCTTGTATCAT (SEQ ID NO. 175) |
| 175 | CCAGGCGCTTAATCATTGTGAATTACAGGTAG (SEQ ID NO. 176) |
| 176 | CGCCTGATGGAAGTTTCCATTAAACATAACCG (SEQ ID NO. 177) |
| 177 | TTTCATGAAAATTGTGTCGAAATCTGTACAGA (SEQ ID NO. 178) |
| 178 | ATATATTCTTTTTTCACGTTGAAAATAGTTAG (SEQ ID NO. 179) |
| 179 | AATAATAAGGTCGCTGAGGCTTGCAAAGACTT (SEQ ID NO. 180) |
| 180 | CGTAACGATCTAAAGTTTTGTCGTGAATTGCG (SEQ ID NO. 181) |
| 181 | ACCCAAATCAAGTTTTTTGGGGTCAAAGAACG (SEQ ID NO. 182) |
| 182 | TGGACTCCCTTTTCACCAGTGAGACCTGTCGT (SEQ ID NO. 183) |
| 183 | TGGTTTTTAACGTCAAAGGGCGAAGAACCATC (SEQ ID NO. 184) |
| 184 | GCCAGCTGCCTGCAGGTCGACTCTGCAAGGCG (SEQ ID NO. 185) |
| 185 | CTTGCATGCATTAATGAATCGGCCCGCCAGGG (SEQ ID NO. 186) |
| 186 | ATTAAGTTCGCATCGTAACCGTGCGAGTAACA (SEQ ID NO. 187) |
| 187 | TAGATGGGGGGTAACGCCAGGGTTGTGCCAAG (SEQ ID NO. 188) |
| 188 | ACCCGTCGTCATATGTACCCCGGTAAAGGCTA (SEQ ID NO. 189) |
| 189 | CATGTCAAGATTCTCCGTGGGAACCGTTGGTG (SEQ ID NO. 190) |
| 190 | TCAGGTCACTTTTGCGGGAGAAGCAGAATTAG (SEQ ID NO. 191) |
| 191 | CTGTAATATTGCCTGAGAGTCTGGAAAACTAG (SEQ ID NO. 192) |
| 192 | CAAAATTAAAGTACGGTGTCTGGAAGAGGTCA (SEQ ID NO. 193) |
| 193 | TGCAACTAAGCAATAAAGCCTCAGTTATGACC (SEQ ID NO. 194) |
| 194 | TTTTTGCGCAGAAAACGAGAATGAATGTTTAG (SEQ ID NO. 195) |
| 195 | AAACAGTTGATGGCTTAGAGCTTATTTAAATA (SEQ ID NO. 196) |
| 196 | ACTGGATAACGGAACAACATTATTACCTTATG (SEQ ID NO. 197) |
| 197 | ACGAACTAGCGTCCAATACTGCGGAATGCTTT (SEQ ID NO. 198) |
| 198 | CGATTTTAGAGGACAGATGAACGGCGCGACCT (SEQ ID NO. 199) |
| 199 | CTTTGAAAAGAACTGGCTCATTATTTAATAAA (SEQ ID NO. 200) |
| 200 | GCTCCATGAGAGGCTTTGAGGACTAGGGAGTT (SEQ ID NO. 201) |
| 201 | ACGGCTACTTACTTAGCCGGAACGCTGACCAA (SEQ ID NO. 202) |
| 202 | AAAGGCCGAAAGGAACAACTAAAGCTTTCCAG (SEQ ID NO. 203) |
| 203 | GAGAATAGCTTTTGCGGGATCGTCGGGTAGCA (SEQ ID NO. 204) |
| 204 | ACGTTAGTAAATGAATTTTCTGTAAGCGGAGT (SEQ ID NO. 205) |
| 205 | TTTTCGATGGCCCACTACGTAAACCGTC (SEQ ID NO. 206) |
| 206 | TATCAGGGTTTTCGGTTTGCGTATTGGGAACGCGCG (SEQ ID NO. 207) |
| 207 | GGGAGAGGTTTTTGTAAAACGACGGCCATTCCCAGT (SEQ ID NO. 208) |
| 208 | CACGACGTTTTTGTAATGGGATAGGTCAAAACGGCG (SEQ ID NO. 209) |
| 209 | GATTGACCTTTTGATGAACGGTAATCGTAGCAAACA (SEQ ID NO. 210) |
| 210 | AGAGAATCTTTTGGTTGTACCAAAAACAAGCATAAA (SEQ ID NO. 211) |

TABLE 2-continued

Staple sequences of DNA origami:

| Name | Sequence |
|---|---|
| 211 | GCTAAATCTTTTCTGTAGCTCAACATGTATTGCTGA (SEQ ID NO. 212) |
| 212 | ATATAATGTTTTCATTGAATCCCCCTCAAATCGTCA (SEQ ID NO. 213) |
| 213 | TAAATATTTTTTGGAAGAAAAATCTACGACCAGTCA (SEQ ID NO. 214) |
| 214 | GGACGTTGTTTTCATAAGGGAACCGAAAGGCGCAG (SEQ ID NO. 215) |
| 215 | ACGGTCAATTTTGACAGCATCGGAACGAACCCTCAG (SEQ ID NO. 216) |
| 216 | CAGCGAAAATTTTACTTTCAACAGTTTCTGGGATTTTGCTAAACTTTT (SEQ ID NO. 217) |
| rt-rem1 | AACATCACTTGCCTGAGTAGAAGAACT (SEQ ID NO. 218) |
| rt-rem2 | TGTAGCAATACTTCTTTGATTAGTAAT (SEQ ID NO. 219) |
| rt-rem3 | AGTCTGTCCATCACGCAAATTAACCGT (SEQ ID NO. 220) |
| rt-rem4 | ATAATCAGTGAGGCCACCGAGTAAAAG (SEQ ID NO. 221) |
| rt-rem5 | ACGCCAGAATCCTGAGAAGTGTTTTT (SEQ ID NO. 222) |
| rt-rem6 | TTAAAGGGATTTTAGACAGGAACGGT (SEQ ID NO. 223) |
| rt-rem7 | AGAGCGGGAGCTAAACAGGAGGCCGA (SEQ ID NO. 224) |
| rt-rem8 | TATAACGTGCTTTCCTCGTTAGAATC (SEQ ID NO. 225) |
| rt-rem9 | GTACTATGGTTGCTTTGACGAGCACG (SEQ ID NO. 226) |
| rt-rem10 | GCGCTTAATGCGCCGCTACAGGGCGC (SEQ ID NO. 227) |

FRET Labeled Staples:

89-TAMRA:
(SEQ ID NO: 228)
AGAGGCATAATTTCATCTTCTGACTAT/i6-TAMN/AACTA

91-Fluorescein:
(SEQ ID NO: 229)
TATGTAAACCTTT/iFluorT/TTAATGGAAAAATTACCT

Biotin Labeled Staples:

77-biotin:
(SEQ ID NO. 230)
TGCTCAGTCAGTCTCT GAATTTACCAGGAGGT TTTTT /3Bio/

78-biotin:
(SEQ ID NO. 231)
GGAAAGCGACCAGGCG GATAAGTGAATAGGTG TTTTT /3Bio/

79-biotin:
(SEQ ID NO. 232)
TGAGGCAGGCGTCAGA CTGTAGCGTAGCAAGG TTTTT /3Bio/

80-biotin:
(SEQ ID NO. 233)
TGCCTTTAGTCAGACG ATTGGCCTGCCAGAAT TTTTT /3Bio/

TABLE 3

Staples with probes for TCRα mRNA:

| | |
|---|---|
| A'-73-1 | GCCACGCTATACGTGG TTTGAAGATATCTTG (SEQ ID NO. 234) |
| A'-73-2 | GGTGGCGTTGGTCTC CACAGACAACGCTCAT (SEQ ID NO. 235) |
| A'-69-1 | GCGCAGAGATATCAAA TTTGAAGATATCTTG (SEQ ID NO. 236) |
| A'-69-2 | GGTGGCGTTGGTCTC ATTATTTGACATTATC (SEQ ID NO. 237) |
| A'-65-1 | CATATTTAGAAATACC TTTGAAGATATCTTG (SEQ ID NO. 238) |
| A'-65-2 | GGTGGCGTTGGTCTC GACCGTGTTACCTTTT (SEQ ID NO. 239) |
| A'-61-1 | TTTTGTTTAAGCCTTA TTTGAAGATATCTTG (SEQ ID NO. 240) |
| A'-61-2 | GGTGGCGTTGGTCTC AATCAAGAATCGAGAA (SEQ ID NO. 241) |
| A'-57-1 | AATCACCAAATAGAAA TTTGAAGATATCTTG (SEQ ID NO. 242) |
| A'-57-2 | GGTGGCGTTGGTCTC ATTCATATATAACGGA (SEQ ID NO. 243) |
| A'-53-1 | CCTCAAGAATACATGG TTTGAAGATATCTTG (SEQ ID NO. 244) |
| A'-53-2 | GGTGGCGTTGGTCTC CTTTTGATAGAACCAC (SEQ ID NO. 245) |

Staples with probes for TCRβ mRNA:

| | |
|---|---|
| B'-158-1 | AGTTTGGAGCCCTTCA GTGTGACAGGTTTGG (SEQ ID NO. 246) |
| B'-158-2 | CTGCACTGATGTTCT CCGCCTGGTTGCGCTC (SEQ ID NO. 247) |
| B'-162-1 | CAGCTGGCGGACGACG GTGTGACAGGTTTGG (SEQ ID NO. 248) |
| B'-162-2 | CTGCACTGATGTTCT ACAGTATCGTAGCCAG (SEQ ID NO. 249) |
| B'-166-1 | GGTAGCTAGGATAAAA GTGTGACAGGTTTGG (SEQ ID NO. 250) |
| B'-166-2 | CTGCACTGATGTTCT ATTTTTAGTTAACATC (SEQ ID NO. 251) |
| B'-170-1 | TACCTTTAAGGTCTTT GTGTGACAGGTTTGG (SEQ ID NO. 252) |

TABLE 3-continued

| | |
|---|---|
| B'-170-2 | CTGCACTGATGTTCT ACCCTGACAAAGAAGT (SEQ ID NO. 253) |
| B'-174-1 | TTTCAACTATAGGCTG GTGTGACAGGTTTGG (SEQ ID NO. 254) |
| B'-174-2 | CTGCACTGATGTTCT GCTGACCTTGTATCAT (SEQ ID NO. 255) |

TABLE 3-continued

| | |
|---|---|
| B'-178-1 | ATATATTCTTTTTTCA GTGTGACAGGTTTGG (SEQ ID NO. 256) |
| B'-178-2 | CTGCACTGATGTTCT CGTTGAAAATAGTTAG (SEQ ID NO. 257) |

TABLE 4

Primers for reverse transcription linking reaction:

CbetaRT
ACAAGGAGACCTTGGGTGGA (SEQ ID NO. 258)

Vbeta1RT
Phos'CAGGTGCAGTACAAGGTTCTAGTGTTCTAGTGTATTCTGTTCCGTCTTTCGT
TCTAGCTTGCTGCCTTCTTTTGTCGATAACGTATCGTACCCGTTTAATGGACACTT
CCTCATGAGACAGTATCAGAGATCAATTTAGTCCTCAAAGAGTTACTCGTAGTTGC
TACGCTCGTTCCGA TGCGAGGATCTTTTAACTGGTA (SEQ ID NO. 259)

Vbeta2RT
Phos'CTGCTGGCACAGAAGTATGTAGTGTTCTAGTGTATTCTGTTCCGTCTTTCGT
TCTAGCTTGCTGCCTTCTTTTGTCGATAACGTATCGTACCCGTTTAATGGACACTT
CCTCATGAGACAGTATCAGAGATCAATTTAGTCCTCAAAGAGTTACTCGTAGTTGC
TACGCTCGTTCCGA TGCGAGGATCTTTTAACTGGTA (SEQ ID NO. 260)

Vbeta3RT
Phos'GCTAAGCTGCTGGCACAGAAAGTGTTCTAGTGTATTCTGTTCCGTCTTTCGT
TCTAGCTTGCTGCCTTCTTTTGTCGATAACGTATCGTACCCGTTTAATGGACACTT
CCTCATGAGACAGTATCAGAGATCAATTTAGTCCTCAAAGAGTTACTCGTAGTTGC
TACGCTCGTTCCGA TGCGAGGATCTTTTAACTGGTA (SEQ ID NO. 261)

Vbeta4RT
Phos'TCTTAGCTGCTGGCACAGAGAGTGTTCTAGTGTATTCTGTTCCGTCTTTCGT
TCTAGCTTGCTGCCTTCTTTTGTCGATAACGTATCGTACCCGTTTAATGGACACTT
CCTCATGAGACAGTATCAGAGATCAATTTAGTCCTCAAAGAGTTACTCGTAGTTGC
TACGCTCGTTCCGA TGCGAGGATCTTTTAACTGGTA (SEQ ID NO. 262)

Vbeta5RT
Phos'TCTTGGCTGCTGGCACAAAAAGTGTTCTAGTGTATTCTGTTCCGTCTTTCGT
TCTAGCTTGCTGCCTTCTTTTGTCGATAACGTATCGTACCCGTTTAATGGACACTT
CCTCATGAGACAGTATCAGAGATCAATTTAGTCCTCAAAGAGTTACTCGTAGTTGC
TACGCTCGTTCCGA TGCGAGGATCTTTTAACTGGTA (SEQ ID NO. 263)

Vbeta12RT
Phos'AGAGCTGGCACAGAAGTACAAGTGTTCTAGTGTATTCTGTTCCGTCTTTCGT
TCTAGCTTGCTGCCTTCTTTTGTCGATAACGTATCGTACCCGTTTAATGGACACTT
CCTCATGAGACAGTATCAGAGATCAATTTAGTCCTCAAAGAGTTACTCGTAGTTGC
TACGCTCGTTCCGA TGCGAGGATCTTTTAACTGGTA (SEQ ID NO. 264)

Vbeta13RT
Phos'CATCACTGCTGGCACAGAAAGTGTTCTAGTGTATTCTGTTCCGTCTTTCGTT
CTAGCTTGCTGCCTTCTTTTGTCGATAACGTATCGTACCCGTTTAATGGACACTTC
CTCATGAGACAGTATCAGAGATCAATTTAGTCCTCAAAGAGTTACTCGTAGTTGCT
ACGCTCGTTCCGA TGCGAGGATCTTTTAACTGGTA (SEQ ID NO. 265)

Vbeta14RT
Phos'AGAAACTGCTGGCACAGAGAAGTGTTCTAGTGTATTCTGTTCCGTCTTTCGT
TCTAGCTTGCTGCCTTCTTTTGTCGATAACGTATCGTACCCGTTTAATGGACACTT
CCTCATGAGACAGTATCAGAGATCAATTTAGTCCTCAAAGAGTTACTCGTAGTTGC
TACGCTCGTTCCGA TGCGAGGATCTTTTAACTGGTA (SEQ ID NO. 266)

Vbeta15RT
Phos'GCTAAACTGCTGGCACACAAGTGTTCTAGTGTATTCTGTTCCGTCTTTCGTT
CTAGCTTGCTGCCTTCTTTTGTCGATAACGTATCGTACCCGTTTAATGGACACTTC
CTCATGAGACAGTATCAGAGATCAATTTAGTCCTCAAAGAGTTACTCGTAGTTGCT
ACGCTCGTTCCGA TGCGAGGATCTTTTAACTGGTA (SEQ ID NO. 267)

Vbeta16RT
Phos'TCTAAGCTGCTTGCACAAAGAGTGTTCTAGTGTATTCTGTTCCGTCTTTCGTT
CTAGCTTGCTGCCTTCTTTTGTCGATAACGTATCGTACCCGTTTAATGGACACTTC
CTCATGAGACAGTATCAGAGATCAATTTAGTCCTCAAAGAGTTACTCGTAGTTGCT
ACGCTCGTTCCGA TGCGAGGATCTTTTAACTGGTA (SEQ ID NO. 268)

Vbeta17RT
Phos'TCTCTACTGCTAGCACAGAGAGTGTTCTAGTGTATTCTGTTCCGTCTTTCGT
TCTAGCTTGCTGCCTTCTTTTGTCGATAACGTATCGTACCCGTTTAATGGACACTT

TABLE 4-continued

Primers for reverse transcription linking reaction:

CCTCATGAGACAGTATCAGAGATCAATTTAGTCCTCAAAGAGTTACTCGTAGTTGC
TACGCTCGTTCCGA TGCGAGGATCTTTTAACTGGTA (SEQ ID NO. 269)

Vbeta19RT
Phos'CTATACTGCTGGCACAGAGAAGTGTTCTAGTGTATTCTGTTCCGTCTTTCGT
TCTAGCTTGCTGCCTTCTTTTGTCGATAACGTATCGTACCCGTTTAATGGACACTT
CCTCATGAGACAGTATCAGAGATCAATTTAGTCCTCAAAGAGTTACTCGTAGTTGC
TACGCTCGTTCCGA TGCGAGGATCTTTTAACTGGTA (SEQ ID NO. 270)

Vbeta20RT
Phos'TCCCTAGCACCACAGAGATAAGTGTTCTAGTGTATTCTGTTCCGTCTTTCGT
TCTAGCTTGCTGCCTTCTTTTGTCGATAACGTATCGTACCCGTTTAATGGACACTT
CCTCATGAGACAGTATCAGAGATCAATTTAGTCCTCAAAGAGTTACTCGTAGTTGC
TACGCTCGTTCCGA TGCGAGGATCTTTTAACTGGTA (SEQ ID NO. 271)

Vbeta23RT
Phos'GATTGACTGCTGGAGCACAAAGTGTTCTAGTGTATTCTGTTCCGTCTTTCGT
TCTAGCTTGCTGCCTTCTTTTGTCGATAACGTATCGTACCCGTTTAATGGACACTT
CCTCATGAGACAGTATCAGAGATCAATTTAGTCCTCAAAGAGTTACTCGTAGTTGC
TACGCTCGTTCCGA TGCGAGGATCTTTTAACTGGTA (SEQ ID NO. 272)

Vbeta24RT
Phos'TACAGACTGCTGGCACAGAGAGTGTTCTAGTGTATTCTGTTCCGTCTTTCGT
TCTAGCTTGCTGCCTTCTTTTGTCGATAACGTATCGTACCCGTTTAATGGACACTT
CCTCATGAGACAGTATCAGAGATCAATTTAGTCCTCAAAGAGTTACTCGTAGTTGC
TACGCTCGTTCCGA TGCGAGGATCTTTTAACTGGTA (SEQ ID NO. 273)

Vbeta26RT
Phos'GACAGACTGCTGGCACAGAGAGTGTTCTAGTGTATTCTGTTCCGTCTTTCGT
TCTAGCTTGCTGCCTTCTTTTGTCGATAACGTATCGTACCCGTTTAATGGACACTT
CCTCATGAGACAGTATCAGAGATCAATTTAGTCCTCAAAGAGTTACTCGTAGTTGC
TACGCTCGTTCCGA TGCGAGGATCTTTTAACTGGTA (SEQ ID NO. 274)

Vbeta29RT
Phos'GCACAGAAGTACACAGATGTAGTGTTCTAGTGTATTCTGTTCCGTCTTTCGT
TCTAGCTTGCTGCCTTCTTTTGTCGATAACGTATCGTACCCGTTTAATGGACACTT
CCTCATGAGACAGTATCAGAGATCAATTTAGTCCTCAAAGAGTTACTCGTAGTTGC
TACGCTCGTTCCGA TGCGAGGATCTTTTAACTGGTA (SEQ ID NO. 275)

Vbeta30RT
Phos'TCTCTAGAACTACAGAAATAAGTGTTCTAGTGTATTCTGTTCCGTCTTTCGTT
CTAGCTTGCTGCCTTCTTTTGTCGATAACGTATCGTACCCGTTTAATGGACACTTC
CTCATGAGACAGTATCAGAGATCAATTTAGTCCTCAAAGAGTTACTCGTAGTTGCT
ACGCTCGTTCCGA TGCGAGGATCTTTTAACTGGTA (SEQ ID NO. 276)

Vbeta31RT
Phos'AGACTCCAGGCACAGAGGTAAGTGTTCTAGTGTATTCTGTTCCGTCTTTCGT
TCTAGCTTGCTGCCTTCTTTTGTCGATAACGTATCGTACCCGTTTAATGGACACTT
CCTCATGAGACAGTATCAGAGATCAATTTAGTCCTCAAAGAGTTACTCGTAGTTGC
TACGCTCGTTCCGA TGCGAGGATCTTTTAACTGGTA (SEQ ID NO. 277)

TABLE 5

Primers for multiplex PCR reaction:

| | |
|---|---|
| CbetaPCR | Phos' GTCACATTTCTCAGATCCTC (SEQ ID NO. 278) |
| Valpha1PCR | Phos' TACCTCTGTGCTGTGAGGGA (SEQ ID NO. 279) |
| Valpha2PCR | Phos' TTACTGCATTGTGACTGACA (SEQ ID NO. 280) |
| Valpha3PCR | Phos' GTACTTCTGCGCAGTCAGTG (SEQ ID NO. 281) |
| Valpha4PCR | Phos' CTGGAGGACTCAGGCACTTA (SEQ ID NO. 282) |
| Valpha5PCR | Phos' CAGCCTGGAGACTCAGCCAT (SEQ ID NO. 283) |
| Valpha6PCR | Phos' GACTCGGCTGTGTACTACTG (SEQ ID NO. 284) |
| Valpha7PCR | Phos' GCTCTCTACCTCTGTGCA (SEQ ID NO. 285) |
| Valpha8PCR | Phos' GCTGTGTACTTCTGTGCTAC (SEQ ID NO. 286) |
| Valpha9PCR | Phos' CTCGGCTGTGTACTTCTGTG (SEQ ID NO. 287) |
| Valpha10PCR | Phos' CATCTACTTCTGTGCAGCA (SEQ ID NO. 288) |
| Valpha11PCR | Phos' CTACATCTGTGTGGTGGGCG (SEQ ID NO. 289) |
| Valpha12PCR | Phos' CAGCTGTCAGACTCTGCCCT (SEQ ID NO. 290) |

TABLE 5-continued

Primers for multiplex PCR reaction:

| | | |
|---|---|---|
| Valpha13PCR | Phos' ACAGACTCAGGCACTTAT | (SEQ ID NO. 291) |
| Valpha14PCR | Phos' TCTCAGCCTGGAGACTCAGC | (SEQ ID NO. 292) |
| Valpha15-1PCR | Phos' TTCTGTGCTCTCTGGGAGCT | (SEQ ID NO. 293) |
| Valpha15-2PCR | Phos' TTCTGCGCTCTCTCGGAACT | (SEQ ID NO. 294) |
| Valpha16PCR | Phos' TATATTTCTGTGCTATG | (SEQ ID NO. 295) |
| Valpha17PCR | Phos' CAAGTACTTCTGTGCACTGG | (SEQ ID NO. 296) |
| Valpha19PCR | Phos' TGTACCTCTGCGCAGCAGGT | (SEQ ID NO. 297) |

By way of further example, a detailed outline of a DNA origami method of multi-mRNA capture from sorted CD8$^+$ T cells is provided as follows in Table 6:

TABLE 6

Day 1

1. Harvest spleen from mouse.
    a. Add 1 mL RPMI-complete media to a 1.5 mL tube and go to the mouse house
    b. Extract spleen from mouse and place into prepared 1.5 mL tube with media, return to lab
2. Digest spleen and lyse RBCs.
    a. Place a 70 μM cell strainer on one half of a petri dish
    b. Pour the spleen/media from the 1.5 mL tube into the strainer
    c. Add ~1 mL RPMI-complete media to the strainer using an eye dropper
    d. Use the base of a plunger from a 3 mL syringe to smash the spleen through the strainer (lift the strainer intermittently to pull the cells/media through the strainer into the petri dish)
    e. Rinse the plunger with ~1 mL RPMI-complete media into the strainer and discard the plunger
    f. Rinse the strainer with ~2 mL RPMI-complete media into the petri dish, discard the strainer
    g. Pipet the cells/media from the petri dish into a labeled 15 mL tube
    h. Rinse the petri dish 2X with ~1 mL RPMI-complete media and add to the 15 mL tube
    i. Centrifuge the tube on Program 1 (1200 rpm, 5 min, 4 C., A = 9, D = 9, bucket = 3668)
    j. Pour off the supernatant and flick the tube to re-suspend the cells
    k. Add 1 mL ACK lysis buffer and incubate 2 min, RT
    l. Add ~7 mL RPMI-complete buffer (bring total volume to ~8 mL) to quench the lysis buffer
    m. Centrifuge on Program 1
    n. Pour off the supernatant and flick the tube to re-suspend the cells
3. Sort splenocytes for CD8$^+$ T cells
    a. Prepare MACS buffer (~20 mL/spleen) in a 100 mL glass bottle
        i. 5 Prepare fresh buffer for experiment
        ii. In a 100 mL glass bottle add 20 mL autoMACS Rinsing Solution
        iii. Add 1 mL MACS BSA Stock Solution
    b. Re-suspend the cells with 750 μL MACS buffer
    c. Add 50 μL MACS CD8a (Ly-2) Microbeads and mix by pipetting
    d. Incubate 30 min, in the 4 C. fridge
    e. After incubation add ~5 mL MACS buffer (total volume ~6 mL)
    f. Centrifuge tube on Program 1
    g. Pour off supernatant and re-suspend the tube by flicking
    h. Rinse the cells with ~5 mL MACS buffer
    i. Centrifuge on Program 1
    j. Pour off the supernatant and re-suspend the cells by flicking
    k. Re-suspend the cells in 1 mL MACS buffer
    l. Set up the MACS column assembly
        i. Make sure the magnet is attached to the stand
        ii. Open a new MACS MS column and place it with the grooves facing outward into one of the slots on the magnet (the column should fit snugly into place)
        iii. If not keeping the non-CD8 cells, place a liquid waste container below the column assembly (if keeping the non-CD8 cells place a 15 mL tube below the column assembly)
    m. Place a 70 μL cell strainer upside down over the top of the column
    n. Prime the column by pipetting 1 mL MACS buffer onto the cell strainer so that it drips into the column (the buffer should elute through the column)
    o. After priming the column pipet the cells onto the strainer so that they pass through the strainer into the column
    p. Rinse the 15 mL tube the cells were in with 1 mL MACS buffer and pipet this onto the strainer and into the column as well, discard the 15 mL tube TABLE 6-continued q. After the sample has eluted through the column, rinse the column by pipetting 1 mL MACS buffer through the strainer into the column
r. Repeat washing with an additional 1 mL MACS buffer
s. After the column stops dripping label a new 15 mL tube with "Mouse strain, CD8+, Date"
t. Elute the $CD8^+$ T cells in one quick step AWAY FROM THE MAGNET!
    i. Remove the column from the magnet and insert it into the labeled 15 mL tube
    ii. Pipet 1 mL MACS buffer directly into the column
    iii. Use the plunger to slowly elute the cells/media through the column and into the 15 mL tube (press the plunger all the way into the base of the column)
    iv. Discard the column/plunger
u. Cap the 15 mL tube with the purified $CD8^+$ T cells and place on ice until use.

4. Transfection of purified $CD8^+$ T cells with DNA origami
    a. Obtain a 96 well round-bottomed plate and label all wells with corresponding sample names
    b. Turn on the ECM 830 BTX electroporator and make sure all settings are as follows:
        i. Mode: LV
        ii. Voltage: 0300 V
        iii. P. Length: 005 ms
        iv. # Pulses: 01
        v. Interval: 200 ms
        vi. Polarity: UNIPOLAR
    c. Open a new BTX electroporation cuvette (Blue Cap, 2 mm Gap), and discard the eye dropper
    d. Pipet 100 µL cells to the cuvette
    e. Pipet 25 µL Origami (50 nM) to the cuvette
    f. Cap the cuvette and electroporate by placing the cuvette into the stand with the metal sides of the cuvette facing the metal terminals of the stand
    g. Close the cuvette stand and hit "Pulse" on the electroporator
    h. After electroporating the sample, remove the cap and use a 20 µL pipettor to remove the sample from the cuvette and pipette into the corresponding well of the 96 well plate.
    i. After removing as much sample as possible from the cuvette, rinse the cuvette with 100 µL Lonza Mouse T cell Nucleofector Media
    j. Use the 20 µL pipettor to remove the media from the cuvette and pipette into the same well of the 96 well plate (the well should now contain 125 µL cells/origami + 100 µL Nucleofector Media)
    k. Repeat process for each sample. Cuvettes can be reused for identical samples, but new cuvettes should be used for samples receiving different treatments. When finished discard all cuvettes
    l. Place lid on 96 well plate and incubate overnight (at least 16 hr) in the 37 C./5% $CO_2$ incubator Day 2

5. Lyse cells and purify DNA origami with bound cellular mRNA
    a. Remove the 96 well plate from the incubator
    b. Centrifuge the plate on Program 4 (1300 rpm, 3 min, 4 C., A = 9, D = 9, Bucket = 3670)
    c. Flick the media from the plate
    d. Re-suspend the cells in 100 µL 1% NP-40 cell lysis buffer
    e. Incubate plate 1 hr, on ice
    f. Prepare one Sigma Prep Spin Column for each sample:
        i. Pipet 50 µL Streptavidin Agarose Resin into a spin column
        ii. Pipet 500 µL 1X TAE-$Mg^{2+}$ into column
        iii. Centrifuge column 10 s, 2000 rpm
        iv. Remove column from tube and discard effluent
        v. Cap the bottom of the column with cap provided from Sigma kit and place column back into tube
    g. Pipet lysate from 96 well plate into column
    h. Shake tube by hand WITHOUT INVERTING TUBE
    i. Incubate samples 30 min, RT, shaking every 10 min by hand
    j. REMOVE CAP FROM COLUMN, and place into a PCR rack so you can use later
    k. Centrifuge column 10 s, 2000 rpm
    l. Wash column 5X:
        i. Pipet 500 µL 1X TAE $Mg^{2+}$ into column
        ii. Centrifuge column 10 s, 2000 rpm
        iii. Discard effluent
    m. After $5^{th}$ wash, cap the bottom of the column with the same cap used previously and place column into a NEW TUBE TABLE 6-continued 6. Reverse transcription
   a. Reverse transcription will take place directly in the column
   b. In a PCR tube prepare the RT master mix using the Qiagen Omniscript RT Kit (note, below recipe is for one sample):
      15 μL H$_2$O
      2 μL Buffer
      2 μL dNTPs
      1 μL Ribolock RNase Inhibitor
      1 μL CbetaRT primer (100 μM)
      3 μL Linker primer (10-15 μM)
      1 μL Reverse Transcriptase 25 μL Total Volume
   c. Mix the master mix by pipetting, and pipet mix directly into the CAPPED sample column
   d. Incubate 1 hr, 37 C. heat block (block should be set to ~40 C. to account for heat loss through the tube)
7. Ligation
   a. Remove column from heat block
   b. Ligation will also take place directly in the column
   c. In a PCR tube prepare the ligation master mix using the New England Biolabs T4 DNA Ligase Kit (note, below recipe is for one sample):
      7 μL Buffer
      2 μL T4 DNA Ligase 9 μL Total Volume
   d. Mix master mix by pipetting, and pipet mix directly into the sample column
   e. Incubate 1 hr, RT
8. Elution of cDNA
   a. REMOVE CAP FROM SAMPLE
   b. Incubate the column 5 min, 95 C. heat block
   c. Centrifuge column 30 s, 2000 rpm (eluted cDNA will be in tube)
   d. Discard column and keep cDNA on ice until use
9. PCR
   a. PCR reactions will be performed in standard PCR tubes using Phire Green Hot Start II DNA Polymerase Kit
   b. If running multiple samples, prepare one master mix and distribute to individual PCR tubes and then add cDNA sample to each tube individually (note, below recipe is for one sample)
      9.5 μL H$_2$O
      4 μL Buffer
      2 μL dNTPs
      0.5 μL DMSO
      0.75 μL CbetaPCR primer (100 μM)
      0.75 μL Valpha PCR primer (100 μM)
      0.70 μL DNA Polymerase
      18.2 μL +
      2 μL cDNA Sample 20.2 μL Total Volume
   c. Mix PCR sample by pipetting (be sure to remove any air bubbles)
   d. Set up the following program on the thermocycler:
      98 C.-30 s
      98 C.-5 s      } 30-40 cycles
      45 C.-7 s
      72 C.-7 s
      72 C.-60 s
      4 C.-Hold
10. Analyze products by gel electrophoresis (and/or sequencing)
    a. Prepare a 2% agarose gel while the PCR reaction is running
    b. Measure 1 g agarose on the scale and add to a 125 mL Erlenmeyer flask
    c. Measure out 50 mL 1× TAE buffer in a 50 mL tube and add to the flask
    d. Microwave the flask for 90 s (Be careful, flask will be extremely hot!)
    e. Set up gel box/cassette
    f. Pour the gel from the flask into the cassette, remove any bubbles with a pipette tip
    g. Insert the 10 tooth comb with the 1.5 mm width into the grooves on the top of the gel cassette (the teeth of the comb should penetrate just below the surface of the gel)
    h. Let gel cool/harden for at least 30 min
    i. Remove comb from gel
    j. Remove gel cassette from gel box and place the wells on the negative (black) terminal side
    k. Fill the gel box with 1× TAE so that the buffer covers the gel by at least 2-3 cm.
    l. Prepare PCR samples (Phire Green Polymerase Kit includes gel loading dye in the PCR buffer, so no gel loading dye needs to be added):
       i. Pipet 10 μL 100 bp+ DNA loading ladder into a PCR tube
       ii. To all PCR samples and the ladder add 1 μL SYBR Gold TABLE 6-continued m. Pipet your ladder into the first well of the gel and your PCR samples into the remaining wells (be sure to make a diagram in your lab book of which wells correspond to which samples)
   n. Run the gel for 1 hr, 110 V
   o. Remove the gel cassette from the gel box and place on the UV imager
   p. Open the program AlphaImager HP
   q. Hit Acquire and adjust to the following settings:
      i. Aperture = 1.20
      ii. Zoom = 25.00
      iii. Focus = 1.80
      iv. Be sure Auto Expose is NOT checked and set exposure time manually to 0:800
      v. Be sure Auto Focus is NOT checked and that NONE of the display boxes are checked
      vi. Make sure Transillumination is set to UV
      vii. Make sure NEITHER of the EPI/Reflective settings are on
      viii. Make sure the Lens is set to 3 (SYBR Green)
   r. Open the door and adjust the gel placement so that the wells are at the top of the screen and the whole gel is visible
   s. Close the door and hit Acquire
   t. You can adjust the White and Gamma contrasts to make the image clearer if necessary
   u. When finished, click "File → Save Modified → Save Modified Grayscale"
   v. Save the file into your folder as follows "MM.DD.YY Expt Title"
   w. Discard gel and clean up all work areas While the preferred embodiments of the present invention have been illustrated in detail, it should be apparent that modifications and adaptations to those embodiments may occur to one skilled in the art without departing from the scope of the present invention as set forth in the following claims.

What is claimed is:

1. A method for sequencing genetic information from individual cells within a mixed population of cells without single-cell sorting, comprising the steps of:
   (a) transfecting a cell with a DNA origami nanostructure;
   (b) isolating said DNA origami nanostructure from said transfected cell, wherein the DNA origami nanostructure is bound to complementary RNA from said cell;
   (c) reverse transcribing said RNA into complementary DNA (cDNA); and
   (d) sequencing said complementary DNA.

2. A method for obtaining both TCR alpha and beta CDR3 mRNA sequences from individual cells within a mixed population of cells without single-cell sorting, comprising the steps of:
   (a) transfecting a primary T cell with a DNA origami nanostructure having a sequence complementary to TCR alpha and beta constant region mRNA;
   (b) isolating said DNA origami nanostructure from said transfected cell, wherein the DNA origami nanostructure is bound to said sequences of complementary mRNA from said cell;
   (c) reverse transcribing said mRNA into complementary DNA (cDNA); and
   (d) sequencing said complementary DNA.

3. The method of claim 2, wherein said DNA origami nanostructures are composed of ssDNA M13 phage refolded with complementary ssDNA staple sequences into predetermined shapes with selected staples extended with complementary sequences to TCR alpha and beta constant region mRNA.

4. The method of claim 1, wherein said step of transfecting comprises electroporation.

5. A method for sequencing two or more nucleic acid sequences from individual cells within a mixed population of cells without single-cell sorting, comprising the steps of:
   (a) transfecting a cell with a DNA origami nanostructure;
   (b) isolating said DNA origami nanostructure from said transfected cell, wherein the DNA origami nanostructure is bound to two or more sequences of complementary nucleic acids from said cell; and
   (c) sequencing said two or more sequences of complementary nucleic acids.

6. The method of claim 5, further comprising linking said two or more sequences of complementary nucleic acids into a single DNA molecule and sequencing said DNA.

7. The method of claim 5, wherein said step of transfecting comprises electroporation.

\* \* \* \* \*

```
                        SEQUENCE LISTING

<160> NUMBER OF SEQ ID NOS: 297

<210> SEQ ID NO 1
<211> LENGTH: 7249
<212> TYPE: DNA
<213> ORGANISM: Phage M13

<400> SEQUENCE: 1
aatgctacta ctattagtag aattgatgcc accttttcag ctcgcgcccc aaatgaaaat      60
atagctaaac aggttattga ccatttgcga aatgtatcta atggtcaaac taaatctact     120
cgttcgcaga attgggaatc aactgttata tggaatgaaa cttccagaca ccgtacttta     180
gttgcatatt taaaacatgt tgagctacag cattatattc agcaattaag ctctaagcca     240
tccgcaaaaa tgacctctta tcaaaaggag caattaaagg tactctctaa tcctgacctg     300
ttggagtttg cttccggtct ggttcgcttt gaagctcgaa ttaaaacgcg atatttgaag     360
tctttcgggc ttcctcttaa tctttttgat gcaatccgct ttgcttctga ctataatagt     420
cagggtaaag acctgatttt tgatttatgg tcattctcgt tttctgaact gtttaaagca     480
tttgaggggg attcaatgaa tatttatgac gattccgcag tattggacgc tatccagtct     540
aaacatttta ctattacccc ctctggcaaa acttcttttg caaaagcctc tcgctatttt     600
ggtttttatc gtcgtctggt aaacgagggt tatgatagtg ttgctcttac tatgcctcgt     660
aattcctttt ggcgttatgt atctgcatta gttgaatgtg gtattcctaa atctcaactg     720
atgaatcttt ctacctgtaa taatgttgtt ccgttagttc gttttattaa cgtagatttt     780
tcttcccaac gtcctgactg gtataatgag ccagttctta aaatcgcata aggtaattca     840
caatgattaa agttgaaatt aaaccatctc aagcccaatt tactactcgt tctggtgttt     900
ctcgtcaggg caagccttat tcactgaatg agcagctttt tacgttgat tgggtaatg      960 aatatccggt tcttgtcaag attactcttg atgaaggtca gccagcctat gcgcctggtc    1020
```

```
tgtacaccgt tcatctgtcc tctttcaaag ttggtcagtt cggttcccct atgattgacc    1080
gtctgcgcct cgttccggct aagtaacatg gagcaggtcg cggatttcga cacaatttat    1140
caggcgatga tacaaatctc cgttgtactt tgtttcgcgc ttggtataat cgctggggt     1200 caaagatgag tgttttagtg tattcttttg cctctttcgt tttaggttgg tgccttcgta    1260
gtggcattac gtattttacc cgtttaatgg aaacttcctc atgaaaaagt ctttagtcct    1320
caaagcctct gtagccgttg ctaccctcgt tccgatgctg tctttcgctg ctgagggtga    1380
cgatcccgca aaagcggcct ttaactccct gcaagcctca gcgaccgaat atatcggtta    1440
tgcgtgggcg atggttgttg tcattgtcgg cgcaactatc ggtatcaagc tgtttaagaa    1500
attcacctcg aaagcaagct gataaaccga tacaattaaa ggctcctttt ggagcctttt    1560
ttttggagat tttcaacgtg aaaaaattat tattcgcaat tcctttagtt gttcctttct    1620
attctcactc cgctgaaact gttgaaagtt gtttagcaaa atcccataca gaaaattcat    1680
ttactaacgt ctggaaagac gacaaaactt tagatcgtta cgctaactat gagggctgtc    1740
tgtggaatgc tacaggcgtt gtagtttgta ctggtgacga aactcagtgt tacggtacat    1800
gggttcctat tgggcttgct atccctgaaa atgagggtgg tggctctgag gtggcggtt     1860 ctgagggtgg cggttctgag ggtggcggta ctaaacctcc tgagtacggt gatacaccta    1920
ttccgggcta tacttatatc aaccctctcg acggcactta tccgcctggt actgagcaaa    1980
accccgctaa tcctaatcct tctcttgagg agtctcagcc tcttaatact ttcatgtttc    2040
agaataatag gttccgaaat aggcagggggg cattaactgt ttatacgggc actgttactc    2100
aaggcactga ccccgttaaa acttattacc agtacactcc tgtatcatca aaagccatgt    2160
atgacgctta ctggaacggt aaattcagag actgcgcttt ccattctggc tttaatgagg    2220
atttatttgt ttgtgaatat caaggccaat cgtctgacct gcctcaacct cctgtcaatg    2280
ctggcggcgg ctctggtggt ggttctggtg gcggctctga gggtggtggc tctgagggtg    2340
gcggttctga gggtggcggc tctgagggag gcggttccgg tggtggctct ggttccggtg    2400
attttgatta tgaaaagatg gcaaacgcta ataagggggc tatgaccgaa aatgccgatg    2460
aaaacgcgct acagtctgac gctaaaggca aacttgattc tgtcgctact gattacggtg    2520
ctgctatcga tggtttcatt ggtgacgttt ccggccttgc taatggtaat ggtgctactg    2580
gtgattttgc tggctctaat tcccaaatgg ctcaagtcgg tgacggtgat aattcacctt    2640
taatgaataa tttccgtcaa tatttacctt ccctccctca atcggttgaa tgtcgccctt    2700
ttgtctttgg cgctggtaaa ccatatgaat tttctattga ttgtgacaaa ataaacttat    2760
tccgtggtgt ctttgcgttt cttttatatg ttgccacctt tatgtatgta ttttctacgt    2820
ttgctaacat actgcgtaat aaggagtctt aatcatgcca gttcttttgg gtattccgtt    2880
attattgcgt ttcctcggtt tccttctggt aactttgttc ggctatctgc ttacttttct    2940 taaaagggc ttcggtaaga tagctattgc tatttcattg tttcttgctc ttattattgg     3000
gcttaactca attcttgtgg gttatctctc tgatattagc gctcaattac cctctgactt    3060
tgttcagggt gttcagttaa ttctcccgtc taatgcgctt ccctgttttt atgttattct    3120
ctctgtaaag gctgctattt tcattttttga cgttaaacaa aaaatcgttt cttatttgga    3180
ttgggataaa taatatggct gtttattttg taactggcaa attaggctct ggaaagacgc    3240
tcgttagcgt tggtaagatt caggataaaa ttgtagctgg gtgcaaaata gcaactaatc    3300
ttgatttaag gcttcaaaac ctcccgcaag tcgggaggtt cgctaaaacg cctcgcgttc    3360
```

```
ttagaatacc ggataagcct tctatatctg atttgcttgc tattgggcgc ggtaatgatt    3420
cctacgatga aaataaaaac ggcttgcttg ttctcgatga gtgcggtact tggtttaata    3480
cccgttcttg gaatgataag gaaagacagc cgattattga ttggtttcta catgctcgta    3540
aattaggatg ggatattatt tttcttgttc aggacttatc tattgttgat aaacaggcgc    3600
gttctgcatt agctgaacat gttgtttatt gtcgtcgtct ggacagaatt actttacctt    3660
ttgtcggtac tttatattct cttattactg gctcgaaaat gcctctgcct aaattacatg    3720
ttggcgttgt taaatatggc gattctcaat taagccctac tgttgagcgt tggctttata    3780
ctggtaagaa tttgtataac gcatatgata ctaaacaggc ttttctagt aattatgatt    3840 ccggtgttta ttcttattta acgccttatt tatcacacgg tcggtatttc aaaccattaa    3900
atttaggtca gaagatgaaa ttaactaaaa tatatttgaa aaagttttct cgcgttcttt    3960
gtcttgcgat tggatttgca tcagcattta catatagtta tataacccaa cctaagccgg    4020
aggttaaaaa ggtagtctct cagacctatg atttttgataa attcactatt gactcttctc    4080
agcgtcttaa tctaagctat cgctatgttt tcaaggattc taagggaaaa ttaattaata    4140
gcgacgattt acagaagcaa ggttattcac tcacatatat tgatttatgt actgttttcca    4200 ttaaaaaagg taattcaaat gaaattgtta aatgtaatta attttgtttt cttgatgttt    4260
gtttcatcat cttcttttgc tcaggtaatt gaaatgaata attcgcctct gcgcgatttt    4320
gtaacttggt attcaaagca atcaggcgaa tccgttattg tttctcccga tgtaaaaggt    4380
actgttactg tatattcatc tgacgttaaa cctgaaaatc tacgcaattt ctttatttct    4440
gttttacgtg caaataattt tgatatggta ggttctaacc cttccattat tcagaagtat    4500
aatccaaaca atcaggatta tattgatgaa ttgccatcat ctgataatca ggaatatgat    4560
gataattccg ctccttctgg tggttttcttt gttccgcaaa atgataatgt tactcaaact    4620
tttaaaatta ataacgttcg ggcaaaggat ttaatacgag ttgtcgaatt gtttgtaaag    4680
tctaatactt ctaaatcctc aaatgtatta tctattgacg ctctaatct attagttgtt    4740 agtgctccta aagatatttt agataacctt cctcaattcc tttcaactgt tgatttgcca    4800
actgaccaga tattgattga gggttttgata tttgaggttc agcaaggtga tgctttagat    4860
ttttcatttg ctgctggctc tcagcgtggc actgttgcag gcggtgttaa tactgaccgc    4920
ctcacctctg ttttatcttc tgctggtggt tcgttcggta ttttaatgg cgatgtttta    4980 gggctatcag ttcgcgcatt aaagactaat agccattcaa aaatattgtc tgtgccacgt    5040
attcttacgc tttcaggtca aagggttct atctctgttg ccagaatgt ccctttatt    5100 actggtcgtg tgactggtga atctgccaat gtaaataatc catttcagac gattgagcgt    5160
caaaatgtag gtatttccat gagcgttttt cctgttgcaa tggctggcgg taatattgtt    5220
ctggatatta ccagcaaggc cgatagtttg agttcttcta ctcaggcaag tgatgttatt    5280
actaatcaaa gaagtattgc tacaacggtt aatttgcgtg atggacagac tcttttactc    5340
ggtggcctca ctgattataa aaacacttct caggattctg gcgtaccgtt cctgtctaaa    5400
atccctttaa tcggcctcct gtttagctcc cgctctgatt ctaacgagga agcacgttta    5460
tacgtgctcg tcaaagcaac catagtacgc gccctgtagc ggcgcattaa gcgcggcggg    5520
tgtggtggtt acgcgcagcg tgaccgctac acttgccagc gccctagcgc ccgctccttt    5580
cgctttcttc ccttcctttc tcgccacgtt cgccggcttt cccgtcaag ctctaaatcg    5640 ggggctccct ttagggttcc gatttagtgc tttacggcac ctcgacccca aaaaacttga    5700
tttgggtgat ggttcacgta gtgggccatc gccctgatag acggtttttc gcccttttgac    5760
```

```
gttggagtcc acgttcttta atagtggact cttgttccaa actggaacaa cactcaaccc      5820
tatctcgggc tattcttttg atttataagg gattttgccg atttcggaac caccatcaaa      5880
caggattttc gcctgctggg gcaaaccagc gtggaccgct tgctgcaact ctctcagggc      5940
caggcggtga agggcaatca gctgttgccc gtctcactgg tgaaaagaaa aaccaccctg      6000
gcgcccaata cgcaaaccgc ctctccccgc gcgttggccg attcattaat gcagctggca      6060
cgacaggttt cccgactgga aagcgggcag tgagcgcaac gcaattaatg tgagttagct      6120
cactcattag gcaccccagg ctttacactt tatgcttccg gctcgtatgt tgtgtggaat      6180
tgtgagcgga taacaatttc acacaggaaa cagctatgac catgattacg aattcgagct      6240
cggtacccgg ggatcctcta gagtcgacct gcaggcatgc aagcttggca ctggccgtcg      6300
ttttacaacg tcgtgactgg gaaaaccctg gcgttaccca acttaatcgc cttgcagcac      6360 atccccottt cgccagctgg cgtaatagcg aagaggcccg caccgatcgc ccttcccaac      6420
agttgcgcag cctgaatggc gaatggcgct ttgcctggtt tccggcacca gaagcggtgc      6480
cggaaagctg gctggagtgc gatcttcctg aggccgatac tgtcgtcgtc ccctcaaact      6540
ggcagatgca cggttacgat gcgcccatct acaccaacgt gacctatccc attacggtca      6600
atccgccgtt tgttcccacg gagaatccga cgggttgtta ctcgctcaca tttaatgttg      6660
atgaaagctg gctacaggaa ggccagacgc gaattatttt tgatggcgtt cctattggtt      6720
aaaaaatgag ctgatttaac aaaaatttaa tgcgaatttt aacaaaatat taacgtttac      6780
aatttaaata tttgcttata caatcttcct gtttttgggg cttttctgat tatcaaccgg      6840
ggtacatatg attgacatgc tagttttacg attaccgttc atcgattctc ttgtttgctc      6900
cagactctca ggcaatgacc tgatagcctt tgtagatctc tcaaaaatag ctaccctctc      6960
cggcattaat ttatcagcta aacggttga atatcatatt gatggtgatt tgactgtctc      7020
cggcctttct cacccttttg aatctttacc tacacattac tcaggcattg catttaaaat      7080
atatgagggt tctaaaaatt tttatccttg cgttgaaata aaggcttctc ccgcaaaagt      7140
attacagggt cataatgttt ttggtacaac cgatttagct ttatgctctg aggctttatt      7200 gcttaattt gctaattctt tgccttgcct gtatgattta ttggatgtt                  7249

<210> SEQ ID NO 2
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 2
caagcccaat aggaacccat gtacaaacag tt                                     32

<210> SEQ ID NO 3
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 3
aatgccccgt aacagtgccc gtatctccct ca                                     32

<210> SEQ ID NO 4
<211> LENGTH: 32
<212> TYPE: DNA
```

```
<213> ORGANISM: ARTIFICIAL SEQUENCE
<220> FEATURE:
<223> OTHER INFORMATION: SYNTHETIC SEQUENCE

<400> SEQUENCE: 4
tgccttgact gcctatttcg gaacagggat ag                        32

<210> SEQ ID NO 5
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 5
gagccgcccc accaccggaa ccgcgacgga aa                        32

<210> SEQ ID NO 6
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 6
aaccagagac cctcagaacc gccaggggtc ag                        32

<210> SEQ ID NO 7
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 7
ttattcatag ggaaggtaaa tattcattca gt                        32

<210> SEQ ID NO 8
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 8
cataacccga ggcatagtaa gagcttttta ag                        32

<210> SEQ ID NO 9
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 9
attgagggta aaggtgaatt atcaatcacc gg                        32

<210> SEQ ID NO 10
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 10
aaaagtaata tcttaccgaa gcccttccag ag                        32
```

<210> SEQ ID NO 11
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 11
gcaatagcgc agatagccga acaattcaac cg                                   32

<210> SEQ ID NO 12
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 12
cctaatttac gctaacgagc gtctaatcaa ta                                   32

<210> SEQ ID NO 13
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 13
tcttaccagc cagttacaaa ataaatgaaa ta                                   32

<210> SEQ ID NO 14
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 14
atcggctgcg agcatgtaga aacctatcat at                                   32

<210> SEQ ID NO 15
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 15
ctaatttatc tttccttatc attcatcctg aa                                   32

<210> SEQ ID NO 16
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 16
gcgttataga aaagcctgt ttagaaggcc gg                                    32

<210> SEQ ID NO 17
<211> LENGTH: 32
<212> TYPE: DNA
<213> ORGANISM: ARTIFICIAL SEQUENCE
<220> FEATURE:

<223> OTHER INFORMATION: SYNTHETIC

<400> SEQUENCE: 17
gctcattttc gcattaaatt tttgagctta ga                         32

<210> SEQ ID NO 18
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 18
aattactaca aattcttacc agtaatccca tc                         32

<210> SEQ ID NO 19
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 19
ttaagacgtt gaaaacatag cgataacagt ac                         32

<210> SEQ ID NO 20
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 20
tagaatccct gagaagagtc aataggaatc at                         32

<210> SEQ ID NO 21
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 21
cttttacaca gatgaatata cagtaaacaa tt                         32

<210> SEQ ID NO 22
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 22
tttaacgttc gggagaaaca ataattttcc ct                         32

<210> SEQ ID NO 23
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 23
cgacaactaa gtattagact ttacaatacc ga                         32

```
<210> SEQ ID NO 24
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 24
ggatttagcg tattaaatcc tttgttttca gg                              32

<210> SEQ ID NO 25
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 25
acgaaccaaa acatcgccat taaatggtgg tt                              32

<210> SEQ ID NO 26
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 26
gaacgtggcg agaaaggaag ggaacaaact at                              32

<210> SEQ ID NO 27
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 27
tagccctacc agcagaagat aaaaacattt ga                              32

<210> SEQ ID NO 28
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 28
cggccttgct ggtaatatcc agaacgaact ga                              32

<210> SEQ ID NO 29
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 29
ctcagagcca ccaccctcat tttcctatta tt                              32

<210> SEQ ID NO 30
<211> LENGTH: 32
<212> TYPE: DNA
<213> ORGANISM: ARTIFICIAL SEQUENCE
<220> FEATURE:
<223> OTHER INFORMATION: SYNTHETIC
```

<400> SEQUENCE: 30
ctgaaacagg taataagttt taacccctca ga                          32

<210> SEQ ID NO 31
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 31
agtgtacttg aaagtattaa gaggccgcca cc                          32

<210> SEQ ID NO 32
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 32
gccaccactc ttttcataat caaaccgtca cc                          32

<210> SEQ ID NO 33
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 33
gtttgccacc tcagagccgc caccgataca gg                          32

<210> SEQ ID NO 34
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 34
gacttgagag acaaaagggc gacaagttac ca                          32

<210> SEQ ID NO 35
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 35
agcgccaacc atttgggaat tagattatta gc                          32

<210> SEQ ID NO 36
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 36
gaaggaaaat aagagcaaga aacaacagcc at                          32

<210> SEQ ID NO 37
<211> LENGTH: 32

<210> SEQ ID NO 37
<211> LENGTH: 32 (implied)
<212> TYPE: DNA
<213> ORGANISM: ARTIFICIAL SEQUENCE
<220> FEATURE:
<223> OTHER INFORMATION: SYNTHETIC

<400> SEQUENCE: 37
gcccaatacc gaggaaacgc aataggttta cc      32

<210> SEQ ID NO 38
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 38
attatttaac ccagctacaa ttttcaagaa cg      32

<210> SEQ ID NO 39
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 39
tattttgctc ccaatccaaa taagtgagtt aa      32

<210> SEQ ID NO 40
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 40
ggtattaaga acaagaaaaa taattaaagc ca      32

<210> SEQ ID NO 41
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 41
taagtcctac caagtaccgc actcttagtt gc      32

<210> SEQ ID NO 42
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 42
acgctcaaaa taagaataaa caccgtgaat tt      32

<210> SEQ ID NO 43
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 43
aggcgttaca gtagggctta attgacaata ga          32

<210> SEQ ID NO 44
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 44
atcaaaatcg tcgctattaa ttaacggatt cg          32

<210> SEQ ID NO 45
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 45
ctgtaaatca taggtctgag agacgataaa ta          32

<210> SEQ ID NO 46
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 46
cctgattgaa agaaattgcg tagacccgaa cg          32

<210> SEQ ID NO 47
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 47
acagaaatct tgaatacca agttccttgc tt          32

<210> SEQ ID NO 48
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 48
ttattaatgc cgtcaataga taatcagagg tg          32

<210> SEQ ID NO 49
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 49
agattagatt taaaagtttg agtacacgta aa          32

<210> SEQ ID NO 50
<211> LENGTH: 32
<212> TYPE: DNA
<213> ORGANISM: ARTIFICIAL SEQUENCE

```
<220> FEATURE:
<223> OTHER INFORMATION: SYNTHETIC

<400> SEQUENCE: 50
aggcggtcat tagtctttaa tgcgcaatat ta                              32

<210> SEQ ID NO 51
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 51
gaatggctag tattaacacc gcctcaacta at                              32

<210> SEQ ID NO 52
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 52
ccgccagcca ttgcaacagg aaaaatattt tt                              32

<210> SEQ ID NO 53
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 53
ccctcagaac cgccaccctc agaactgaga ct                              32

<210> SEQ ID NO 54
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 54
cctcaagaat acatggcttt tgatagaacc ac                              32

<210> SEQ ID NO 55
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 55
taagcgtcga aggattagga ttagtaccgc ca                              32

<210> SEQ ID NO 56
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 56
caccagagtt cggtcatagc cccgccagc aa                               32
```

<210> SEQ ID NO 57
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 57
tcggcattcc gccgccagca ttgacgttcc ag                     32

<210> SEQ ID NO 58
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 58
aatcaccaaa tagaaaattc atatataacg ga                     32

<210> SEQ ID NO 59
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 59
tcacaatcgt agcaccatta ccatcgtttt ca                     32

<210> SEQ ID NO 60
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 60
atacccaaga taacccacaa gaataaacga tt                     32

<210> SEQ ID NO 61
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 61
atcagagaaa gaactggcat gattttattt tg                     32

<210> SEQ ID NO 62
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 62
ttttgtttaa gccttaaatc aagaatcgag aa                     32

<210> SEQ ID NO 63
<211> LENGTH: 32
<212> TYPE: DNA
<213> ORGANISM: ARTIFICIAL SEQUENCE
<220> FEATURE:
<223> OTHER INFORMATION: SYNTHETIC

-continued

<400> SEQUENCE: 63
aggttttgaa cgtcaaaaat gaaagcgcta at     32

<210> SEQ ID NO 64
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 64
caagcaagac gcgcctgttt atcaagaatc gc     32

<210> SEQ ID NO 65
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 65
aatgcagacc gttttattt tcatcttgcg gg     32

<210> SEQ ID NO 66
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 66
catatttaga aataccgacc gtgttaccttt tt     32

<210> SEQ ID NO 67
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 67
aatggtttac aacgccaaca tgtagttcag ct     32

<210> SEQ ID NO 68
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 68
taacctccat atgtgagtga ataaacaaaa tc     32

<210> SEQ ID NO 69
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 69
aaatcaatgg cttaggttgg gttactaaat tt     32

<210> SEQ ID NO 70

<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 70
gcgcagagat atcaaaatta tttgacatta tc        32

<210> SEQ ID NO 71
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 71
aacctaccgc gaattattca tttccagtac at        32

<210> SEQ ID NO 72
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 72
attttgcgtc tttaggagca ctaagcaaca gt        32

<210> SEQ ID NO 73
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 73
ctaaaataga acaaagaaac caccagggtt ag        32

<210> SEQ ID NO 74
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 74
gccacgctat acgtggcaca gacaacgctc at        32

<210> SEQ ID NO 75
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 75
gcgtaagaga gagccagcag caaaaaggtt at        32

<210> SEQ ID NO 76
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 76

-continued ggaaatacct acattttgac gctcacctga aa                              32

<210> SEQ ID NO 77
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 77
tatcaccgta ctcaggaggt ttagcggggt tt                              32

<210> SEQ ID NO 78
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 78
tgctcagtca gtctctgaat ttaccaggag gt                              32

<210> SEQ ID NO 79
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 79
ggaaagcgac caggcggata agtgaatagg tg                              32

<210> SEQ ID NO 80
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 80
tgaggcaggc gtcagactgt agcgtagcaa gg                              32

<210> SEQ ID NO 81
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 81
tgcctttagt cagacgattg gcctgccaga at                              32

<210> SEQ ID NO 82
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 82
ccggaaacac accacggaat aagtaagact cc                              32

<210> SEQ ID NO 83
<211> LENGTH: 32
<212> TYPE: DNA

<213> ORGANISM: ARTIFICIAL SEQUENCE
<220> FEATURE:
<223> OTHER INFORMATION: SYNTHETIC

<400> SEQUENCE: 83
acgcaaaggt caccaatgaa accaatcaag tt        32

<210> SEQ ID NO 84
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 84
ttattacggt cagagggtaa ttgaatagca gc        32

<210> SEQ ID NO 85
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 85
tgaacaaaca gtatgttagc aaactaaaag aa        32

<210> SEQ ID NO 86
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 86
ctttacagtt agcgaacctc ccgacgtagg aa        32

<210> SEQ ID NO 87
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 87
gaggcgttag agaataacat aaaagaacac cc        32

<210> SEQ ID NO 88
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 88
tcattacccg acaataaaca acatatttag gc        32

<210> SEQ ID NO 89
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 89
ccagacgagc gcccaatagc aagcaagaac gc        32

<210> SEQ ID NO 90
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 90
agaggcataa tttcatcttc tgactataac ta                          32

<210> SEQ ID NO 91
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 91
ttttagtttt tcgagccagt aataaattct gt                          32

<210> SEQ ID NO 92
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 92
tatgtaaacc ttttttaatg gaaaaattac ct                          32

<210> SEQ ID NO 93
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 93
ttgaattatg ctgatgcaaa tccacaaata ta                          32

<210> SEQ ID NO 94
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 94
gagcaaaaac ttctgaataa tggaagaagg ag                          32

<210> SEQ ID NO 95
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 95
tggattatga agatgatgaa acaaaatttc at                          32

<210> SEQ ID NO 96
<211> LENGTH: 32
<212> TYPE: DNA
<213> ORGANISM: ARTIFICIAL SEQUENCE
<220> FEATURE:

```
<223> OTHER INFORMATION: SYNTHETIC

<400> SEQUENCE: 96
cggaattatt gaaaggaatt gaggtgaaaa at                                32

<210> SEQ ID NO 97
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 97
atcaacagtc atcatattcc tgattgattg tt                                32

<210> SEQ ID NO 98
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 98
ctaaagcaag atagaaccct tctgaatcgt ct                                32

<210> SEQ ID NO 99
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 99
gccaacagtc accttgctga acctgttggc aa                                32

<210> SEQ ID NO 100
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 100
gaaatggatt atttacattg gcagacattc tg                                32

<210> SEQ ID NO 101
<211> LENGTH: 28
<212> TYPE: DNA
<213> ORGANISM: ARTIFICIAL SEQUENCE
<220> FEATURE:
<223> OTHER INFORMATION: SYNTHETIC

<400> SEQUENCE: 101
tttttataag tatagcccgg ccgtcgag                                     28

<210> SEQ ID NO 102
<211> LENGTH: 36
<212> TYPE: DNA
<213> ORGANISM: ARTIFICIAL SEQUENCE
<220> FEATURE:
<223> OTHER INFORMATION: SYNTHETIC

<400> SEQUENCE: 102
agggttgatt ttataaatcc tcattaaatg atattc                            36
```

<210> SEQ ID NO 103
<211> LENGTH: 36
<212> TYPE: DNA
<213> ORGANISM: ARTIFICIAL SEQUENCE
<220> FEATURE:
<223> OTHER INFORMATION: SYNTHETIC

<400> SEQUENCE: 103
acaaacaatt ttaatcagta gcgacagatc gatagc                     36

<210> SEQ ID NO 104
<211> LENGTH: 36
<212> TYPE: DNA
<213> ORGANISM: ARTIFICIAL SEQUENCE
<220> FEATURE:
<223> OTHER INFORMATION: SYNTHETIC

<400> SEQUENCE: 104
agcaccgttt tttaaaggtg gcaacatagt agaaaa                     36

<210> SEQ ID NO 105
<211> LENGTH: 36
<212> TYPE: DNA
<213> ORGANISM: ARTIFICIAL SEQUENCE
<220> FEATURE:
<223> OTHER INFORMATION: SYNTHETIC

<400> SEQUENCE: 105
tacatacatt ttgacgggag aattaactac agggaa                     36

<210> SEQ ID NO 106
<211> LENGTH: 36
<212> TYPE: DNA
<213> ORGANISM: ARTIFICIAL SEQUENCE
<220> FEATURE:
<223> OTHER INFORMATION: SYNTHETIC

<400> SEQUENCE: 106
gcgcattatt ttgcttatcc ggtattctaa atcaga                     36

<210> SEQ ID NO 107
<211> LENGTH: 36
<212> TYPE: DNA
<213> ORGANISM: ARTIFICIAL SEQUENCE
<220> FEATURE:
<223> OTHER INFORMATION: SYNTHETIC

<400> SEQUENCE: 107
tatagaagtt ttcgacaaaa ggtaaagtag agaata                     36

<210> SEQ ID NO 108
<211> LENGTH: 36
<212> TYPE: DNA
<213> ORGANISM: ARTIFICIAL SEQUENCE
<220> FEATURE:
<223> OTHER INFORMATION: SYNTHETIC

<400> SEQUENCE: 108
taaagtactt ttcgcgagaa aactttttat cgcaag                     36

<210> SEQ ID NO 109
<211> LENGTH: 36
<212> TYPE: DNA
<213> ORGANISM: ARTIFICIAL SEQUENCE
<220> FEATURE:
<223> OTHER INFORMATION: SYNTHETIC

<400> SEQUENCE: 109
acaaagaatt ttattaatta catttaacac atcaag                                     36

<210> SEQ ID NO 110
<211> LENGTH: 36
<212> TYPE: DNA
<213> ORGANISM: ARTIFICIAL SEQUENCE
<220> FEATURE:
<223> OTHER INFORMATION: SYNTHETIC

<400> SEQUENCE: 110
aaaacaaatt ttttcatcaa tataatccta tcagat                                     36

<210> SEQ ID NO 111
<211> LENGTH: 36
<212> TYPE: DNA
<213> ORGANISM: ARTIFICIAL SEQUENCE
<220> FEATURE:
<223> OTHER INFORMATION: SYNTHETIC

<400> SEQUENCE: 111
gatggcaatt ttaatcaata tctggtcaca aatatc                                     36

<210> SEQ ID NO 112
<211> LENGTH: 48
<212> TYPE: DNA
<213> ORGANISM: ARTIFICIAL SEQUENCE
<220> FEATURE:
<223> OTHER INFORMATION: SYNTHETIC

<400> SEQUENCE: 112
aaaccctctt ttaccagtaa taaagggat tcaccagtca cacgtttt                         48

<210> SEQ ID NO 113
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 113
ccgaaatccg aaaatcctgt ttgaagccgg aa                                         32

<210> SEQ ID NO 114
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 114
ccagcagggg caaaatccct tataaagccg gc                                         32

<210> SEQ ID NO 115
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 115
gcataaagtt ccacacaaca tacgaagcgc ca                                         32

<210> SEQ ID NO 116
<211> LENGTH: 32

```
<212> TYPE: DNA
<213> ORGANISM: ARTIFICIAL SEQUENCE
<220> FEATURE:
<223> OTHER INFORMATION: SYNTHETIC

<400> SEQUENCE: 116
gctcacaatg taaagcctgg ggtgggtttg cc                                 32

<210> SEQ ID NO 117
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 117
ttcgccattg ccggaaacca ggcattaaat ca                                 32

<210> SEQ ID NO 118
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 118
gcttctggtc aggctgcgca actgtgttat cc                                 32

<210> SEQ ID NO 119
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 119
gttaaaattt taaccaatag gaacccggca cc                                 32

<210> SEQ ID NO 120
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 120
agacagtcat tcaaagggt gagaagctat at                                  32

<210> SEQ ID NO 121
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 121
aggtaaagaa atcaccatca atataatatt tt                                 32

<210> SEQ ID NO 122
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 122
```
tttcatttgg tcaataacct gtttatatcg cg                              32

<210> SEQ ID NO 123
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 123
tcgcaaatgg ggcgcgagct gaaataatgt gt                              32

<210> SEQ ID NO 124
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 124
ttttaattgc ccgaaagact tcaaaacact at                              32

<210> SEQ ID NO 125
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 125
aagaggaacg agcttcaaag cgaagataca tt                              32

<210> SEQ ID NO 126
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 126
ggaattactc gtttaccaga cgacaaaaga tt                              32

<210> SEQ ID NO 127
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 127
gaataaggac gtaacaaagc tgctctaaaa ca                              32

<210> SEQ ID NO 128
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 128
ccaaatcact tgccctgacg agaacgccaa aa                              32

<210> SEQ ID NO 129
<211> LENGTH: 32
<212> TYPE: DNA
<213> ORGANISM: ARTIFICIAL SEQUENCE

```
<220> FEATURE:
<223> OTHER INFORMATION: SYNTHETIC

<400> SEQUENCE: 129
ctcatcttga ggcaaaagaa tacagtgaat tt                                    32

<210> SEQ ID NO 130
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 130
aaacgaaatg accccagcg attattcatt ac                                     32

<210> SEQ ID NO 131
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 131
cttaaacatc agcttgcttt cgagcgtaac ac                                    32

<210> SEQ ID NO 132
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 132
tcggtttagc ttgataccga tagtccaacc ta                                    32

<210> SEQ ID NO 133
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 133
tgagtttcgt caccagtaca aacttaattg ta                                    32

<210> SEQ ID NO 134
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 134
ccccgattta gagcttgacg gggaaatcaa aa                                    32

<210> SEQ ID NO 135
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 135
gaatagccgc aagcggtcca cgctcctaat ga                                    32
```

<210> SEQ ID NO 136
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 136
gagttgcacg agatagggtt gagtaaggga gc                                    32

<210> SEQ ID NO 137
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 137
gtgagctagt ttcctgtgtg aaatttggga ag                                    32

<210> SEQ ID NO 138
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 138
tcatagctac tcacattaat tgcgccctga ga                                    32

<210> SEQ ID NO 139
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 139
ggcgatcgca ctccagccag ctttgccatc aa                                    32

<210> SEQ ID NO 140
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 140
gaagatcggt gcgggcctct tcgcaatcat gg                                    32

<210> SEQ ID NO 141
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 141
aaataatttt aaattgtaaa cgttgatatt ca                                    32

<210> SEQ ID NO 142
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 142
gcaaatatcg cgtctggcct tcctggcctc ag                                  32

<210> SEQ ID NO 143
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 143
accgttctaa atgcaatgcc tgagaggtgg ca                                  32

<210> SEQ ID NO 144
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 144
tatattttag ctgataaatt aatgttgtat aa                                  32

<210> SEQ ID NO 145
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 145
tcaattcttt tagtttgacc attaccagac cg                                  32

<210> SEQ ID NO 146
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 146
cgagtagaac taatagtagt agcaaaccct ca                                  32

<210> SEQ ID NO 147
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 147
gaagcaaaaa agcggattgc atcagataaa aa                                  32

<210> SEQ ID NO 148
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 148
tcagaagcct ccaacaggtc aggatctgcg aa                                  32

<210> SEQ ID NO 149

<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 149
ccaaaatata atgcagatac ataaacacca ga                          32

<210> SEQ ID NO 150
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 150
cattcaacgc gagaggcttt tgcatattat ag                          32

<210> SEQ ID NO 151
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 151
acgagtagtg acaagaaccg gatataccaa gc                          32

<210> SEQ ID NO 152
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 152
agtaatctta aattgggctt gagagaatac ca                          32

<210> SEQ ID NO 153
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 153
gcgaaacatg ccactacgaa ggcatgcgcc ga                          32

<210> SEQ ID NO 154
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 154
atacgtaaaa gtacaacgga gatttcatca ag                          32

<210> SEQ ID NO 155
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 155

```
caatgacact ccaaaaggag ccttacaacg cc                                    32

<210> SEQ ID NO 156
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 156
aaaaaaggac aaccatcgcc cacgcgggta aa                                    32

<210> SEQ ID NO 157
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 157
tgtagcattc cacagacagc cctcatctcc aa                                    32

<210> SEQ ID NO 158
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 158
gtaaagcact aaatcggaac cctagttgtt cc                                    32

<210> SEQ ID NO 159
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 159
agtttggagc ccttcaccgc ctggttgcgc tc                                    32

<210> SEQ ID NO 160
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 160
agctgattac aagagtccac tattgaggtg cc                                    32

<210> SEQ ID NO 161
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 161
actgcccgcc gagctcgaat tcgttattac gc                                    32

<210> SEQ ID NO 162
<211> LENGTH: 32
<212> TYPE: DNA
```

```
<213> ORGANISM: ARTIFICIAL SEQUENCE
<220> FEATURE:
<223> OTHER INFORMATION: SYNTHETIC

<400> SEQUENCE: 162
cccgggtact ttccagtcgg gaaacgggca ac                               32

<210> SEQ ID NO 163
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 163
cagctggcgg acgacgacag tatcgtagcc ag                               32

<210> SEQ ID NO 164
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 164
gtttgaggga aaggggatg tgctagagga tc                                32

<210> SEQ ID NO 165
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 165
ctttcatccc caaaaacagg aagaccggag ag                               32

<210> SEQ ID NO 166
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 166
agaaaagcaa cattaaatgt gagcatctgc ca                               32

<210> SEQ ID NO 167
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 167
ggtagctagg ataaaaattt ttagttaaca tc                               32

<210> SEQ ID NO 168
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 168
caacgcaatt tttgagagat ctactgataa tc                               32
```

<210> SEQ ID NO 169
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 169
caataaatac agttgattcc caatttagag ag                       32

<210> SEQ ID NO 170
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 170
tccatataca tacaggcaag gcaactttat tt                       32

<210> SEQ ID NO 171
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 171
tacctttaag gtctttaccc tgacaaagaa gt                       32

<210> SEQ ID NO 172
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 172
caaaaatcat tgctcctttt gataagtttc at                       32

<210> SEQ ID NO 173
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 173
tttgccagat cagttgagat ttagtggttt aa                       32

<210> SEQ ID NO 174
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 174
aaagattcag ggggtaatag taaaccataa at                       32

<210> SEQ ID NO 175
<211> LENGTH: 32
<212> TYPE: DNA
<213> ORGANISM: ARTIFICIAL SEQUENCE
<220> FEATURE:

<223> OTHER INFORMATION: SYNTHETIC

<400> SEQUENCE: 175
tttcaactat aggctggctg accttgtatc at                              32

<210> SEQ ID NO 176
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 176
ccaggcgctt aatcattgtg aattacaggt ag                              32

<210> SEQ ID NO 177
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 177
cgcctgatgg aagtttccat taaacataac cg                              32

<210> SEQ ID NO 178
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 178
tttcatgaaa attgtgtcga aatctgtaca ga                              32

<210> SEQ ID NO 179
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 179
atatattctt ttttcacgtt gaaaatagtt ag                              32

<210> SEQ ID NO 180
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 180
aataataagg tcgctgaggc ttgcaaagac tt                              32

<210> SEQ ID NO 181
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 181
cgtaacgatc taaagttttg tcgtgaattg cg                              32

<210> SEQ ID NO 182
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 182
acccaaatca agttttttgg ggtcaaagaa cg         32

<210> SEQ ID NO 183
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 183
tggactccct tttcaccagt gagacctgtc gt         32

<210> SEQ ID NO 184
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 184
tggtttttaa cgtcaaaggg cgaagaacca tc         32

<210> SEQ ID NO 185
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 185
gccagctgcc tgcaggtcga ctctgcaagg cg         32

<210> SEQ ID NO 186
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 186
cttgcatgca ttaatgaatc ggcccgccag gg         32

<210> SEQ ID NO 187
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 187
attaagttcg catcgtaacc gtgcgagtaa ca         32

<210> SEQ ID NO 188
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 188
tagatggggg gtaacgccag ggttgtgcca ag    32

<210> SEQ ID NO 189
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 189
acccgtcgtc atatgtaccc cggtaaaggc ta    32

<210> SEQ ID NO 190
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 190
catgtcaaga ttctccgtgg gaaccgttgg tg    32

<210> SEQ ID NO 191
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 191
tcaggtcact tttgcgggag aagcagaatt ag    32

<210> SEQ ID NO 192
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 192
ctgtaatatt gcctgagagt ctggaaaact ag    32

<210> SEQ ID NO 193
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 193
caaaattaaa gtacggtgtc tggaagaggt ca    32

<210> SEQ ID NO 194
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 194
tgcaactaag caataaagcc tcagttatga cc    32

<210> SEQ ID NO 195
<211> LENGTH: 32

<212> TYPE: DNA
<213> ORGANISM: ARTIFICIAL SEQUENCE
<220> FEATURE:
<223> OTHER INFORMATION: SYNTHETIC

<400> SEQUENCE: 195
tttttgcgca gaaaacgaga atgaatgttt ag                          32

<210> SEQ ID NO 196
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 196
aaacagttga tggcttagag cttatttaaa ta                          32

<210> SEQ ID NO 197
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 197
actggataac ggaacaacat tattaccta tg                           32

<210> SEQ ID NO 198
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 198
acgaactagc gtccaatact gcggaatgct tt                          32

<210> SEQ ID NO 199
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 199
cgattttaga ggacagatga acggcgcgac ct                          32

<210> SEQ ID NO 200
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 200
ctttgaaaag aactggctca ttatttaata aa                          32

<210> SEQ ID NO 201
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 201
gctccatgag aggctttgag gactagggag tt                                         32

<210> SEQ ID NO 202
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 202
acggctactt acttagccgg aacgctgacc aa                                         32

<210> SEQ ID NO 203
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 203
aaaggccgaa aggaacaact aaagctttcc ag                                         32

<210> SEQ ID NO 204
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 204
gagaatagct tttgcgggat cgtcgggtag ca                                         32

<210> SEQ ID NO 205
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 205
acgttagtaa atgaattttc tgtaagcgga gt                                         32

<210> SEQ ID NO 206
<211> LENGTH: 28
<212> TYPE: DNA
<213> ORGANISM: ARTIFICIAL SEQUENCE
<220> FEATURE:
<223> OTHER INFORMATION: SYNTHETIC

<400> SEQUENCE: 206
ttttcgatgg cccactacgt aaaccgtc                                              28

<210> SEQ ID NO 207
<211> LENGTH: 36
<212> TYPE: DNA
<213> ORGANISM: ARTIFICIAL SEQUENCE
<220> FEATURE:
<223> OTHER INFORMATION: SYNTHETIC

<400> SEQUENCE: 207
tatcagggtt ttcggtttgc gtattgggaa cgcgcg                                     36

<210> SEQ ID NO 208
<211> LENGTH: 36
<212> TYPE: DNA
<213> ORGANISM: ARTIFICIAL SEQUENCE

```
<220> FEATURE:
<223> OTHER INFORMATION: SYNTHETIC

<400> SEQUENCE: 208
gggagaggtt tttgtaaaac gacggccatt cccagt                                  36

<210> SEQ ID NO 209
<211> LENGTH: 36
<212> TYPE: DNA
<213> ORGANISM: ARTIFICIAL SEQUENCE
<220> FEATURE:
<223> OTHER INFORMATION: SYNTHETIC

<400> SEQUENCE: 209
cacgacgttt ttgtaatggg ataggtcaaa acggcg                                  36

<210> SEQ ID NO 210
<211> LENGTH: 36
<212> TYPE: DNA
<213> ORGANISM: ARTIFICIAL SEQUENCE
<220> FEATURE:
<223> OTHER INFORMATION: SYNTHETIC

<400> SEQUENCE: 210
gattgacctt ttgatgaacg gtaatcgtag caaaca                                  36

<210> SEQ ID NO 211
<211> LENGTH: 36
<212> TYPE: DNA
<213> ORGANISM: ARTIFICIAL SEQUENCE
<220> FEATURE:
<223> OTHER INFORMATION: SYNTHETIC

<400> SEQUENCE: 211
agagaatctt ttggttgtac caaaaacaag cataaa                                  36

<210> SEQ ID NO 212
<211> LENGTH: 36
<212> TYPE: DNA
<213> ORGANISM: ARTIFICIAL SEQUENCE
<220> FEATURE:
<223> OTHER INFORMATION: SYNTHETIC

<400> SEQUENCE: 212
gctaaatctt ttctgtagct caacatgtat tgctga                                  36

<210> SEQ ID NO 213
<211> LENGTH: 36
<212> TYPE: DNA
<213> ORGANISM: ARTIFICIAL SEQUENCE
<220> FEATURE:
<223> OTHER INFORMATION: SYNTHETIC

<400> SEQUENCE: 213
atataatgtt ttcattgaat cccctcaaa tcgtca                                   36

<210> SEQ ID NO 214
<211> LENGTH: 36
<212> TYPE: DNA
<213> ORGANISM: ARTIFICIAL SEQUENCE
<220> FEATURE:
<223> OTHER INFORMATION: SYNTHETIC

<400> SEQUENCE: 214
taaatatttt ttggaagaaa aatctacgac cagtca                                  36
```

<210> SEQ ID NO 215
<211> LENGTH: 36
<212> TYPE: DNA
<213> ORGANISM: ARTIFICIAL SEQUENCE
<220> FEATURE:
<223> OTHER INFORMATION: SYNTHETIC

<400> SEQUENCE: 215
ggacgttgtt tttcataagg gaaccgaaag gcgcag                36

<210> SEQ ID NO 216
<211> LENGTH: 36
<212> TYPE: DNA
<213> ORGANISM: ARTIFICIAL SEQUENCE
<220> FEATURE:
<223> OTHER INFORMATION: SYNTHETIC

<400> SEQUENCE: 216
acggtcaatt ttgacagcat cggaacgaac cctcag                36

<210> SEQ ID NO 217
<211> LENGTH: 48
<212> TYPE: DNA
<213> ORGANISM: ARTIFICIAL SEQUENCE
<220> FEATURE:
<223> OTHER INFORMATION: SYNTHETIC

<400> SEQUENCE: 217
cagcgaaaat tttactttca acagtttctg ggattttgct aaactttt                48

<210> SEQ ID NO 218
<211> LENGTH: 27
<212> TYPE: DNA
<213> ORGANISM: ARTIFICIAL SEQUENCE
<220> FEATURE:
<223> OTHER INFORMATION: SYNTHETIC

<400> SEQUENCE: 218
aacatcactt gcctgagtag aagaact                27

<210> SEQ ID NO 219
<211> LENGTH: 27
<212> TYPE: DNA
<213> ORGANISM: ARTIFICIAL SEQUENCE
<220> FEATURE:
<223> OTHER INFORMATION: SYNTHETIC

<400> SEQUENCE: 219
tgtagcaata cttctttgat tagtaat                27

<210> SEQ ID NO 220
<211> LENGTH: 27
<212> TYPE: DNA
<213> ORGANISM: ARTIFICIAL SEQUENCE
<220> FEATURE:
<223> OTHER INFORMATION: SYNTHETIC

<400> SEQUENCE: 220
agtctgtcca tcacgcaaat taaccgt                27

<210> SEQ ID NO 221
<211> LENGTH: 27
<212> TYPE: DNA
<213> ORGANISM: ARTIFICIAL SEQUENCE
<220> FEATURE:
<223> OTHER INFORMATION: SYNTHETIC

<400> SEQUENCE: 221
ataatcagtg aggccaccga gtaaaag                                           27

<210> SEQ ID NO 222
<211> LENGTH: 26
<212> TYPE: DNA
<213> ORGANISM: ARTIFICIAL SEQUENCE
<220> FEATURE:
<223> OTHER INFORMATION: SYNTHETIC

<400> SEQUENCE: 222
acgccagaat cctgagaagt gttttt                                            26

<210> SEQ ID NO 223
<211> LENGTH: 26
<212> TYPE: DNA
<213> ORGANISM: ARTIFICIAL SEQUENCE
<220> FEATURE:
<223> OTHER INFORMATION: SYNTHETIC

<400> SEQUENCE: 223
ttaaagggat tttagacagg aacggt                                            26

<210> SEQ ID NO 224
<211> LENGTH: 26
<212> TYPE: DNA
<213> ORGANISM: ARTIFICIAL SEQUENCE
<220> FEATURE:
<223> OTHER INFORMATION: SYNTHETIC

<400> SEQUENCE: 224
agagcgggag ctaaacagga ggccga                                            26

<210> SEQ ID NO 225
<211> LENGTH: 26
<212> TYPE: DNA
<213> ORGANISM: ARTIFICIAL SEQUENCE
<220> FEATURE:
<223> OTHER INFORMATION: SYNTHETIC

<400> SEQUENCE: 225
tataacgtgc tttcctcgtt agaatc                                            26

<210> SEQ ID NO 226
<211> LENGTH: 26
<212> TYPE: DNA
<213> ORGANISM: ARTIFICIAL SEQUENCE
<220> FEATURE:
<223> OTHER INFORMATION: SYNTHETIC

<400> SEQUENCE: 226
gtactatggt tgctttgacg agcacg                                            26

<210> SEQ ID NO 227
<211> LENGTH: 26
<212> TYPE: DNA
<213> ORGANISM: ARTIFICIAL SEQUENCE
<220> FEATURE:
<223> OTHER INFORMATION: SYNTHETIC

<400> SEQUENCE: 227
gcgcttaatg cgccgctaca gggcgc                                            26

<210> SEQ ID NO 228

<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 228
agaggcataa tttcatcttc tgactataac ta                              32

<210> SEQ ID NO 229
<211> LENGTH: 32
<212> TYPE: DNA
<213> ORGANISM: ARTIFICIAL SEQUENCE
<220> FEATURE:
<223> OTHER INFORMATION: SYNTHETIC

<400> SEQUENCE: 229
tatgtaaacc ttttttaatg gaaaaattac ct                              32

<210> SEQ ID NO 230
<211> LENGTH: 37
<212> TYPE: DNA
<213> ORGANISM: ARTIFICIAL SEQUENCE
<220> FEATURE:
<223> OTHER INFORMATION: SYNTHETIC

<400> SEQUENCE: 230
tgctcagtca gtctctgaat ttaccaggag gttttttt                        37

<210> SEQ ID NO 231
<211> LENGTH: 37
<212> TYPE: DNA
<213> ORGANISM: ARTIFICIAL SEQUENCE
<220> FEATURE:
<223> OTHER INFORMATION: SYNTHETIC

<400> SEQUENCE: 231
ggaaagcgac caggcggata agtgaatagg tgttttt                         37

<210> SEQ ID NO 232
<211> LENGTH: 37
<212> TYPE: DNA
<213> ORGANISM: ARTIFICIAL SEQUENCE
<220> FEATURE:
<223> OTHER INFORMATION: SYNTHETIC

<400> SEQUENCE: 232
tgaggcaggc gtcagactgt agcgtagcaa ggttttt                         37

<210> SEQ ID NO 233
<211> LENGTH: 37
<212> TYPE: DNA
<213> ORGANISM: ARTIFICIAL SEQUENCE
<220> FEATURE:
<223> OTHER INFORMATION: SYNTHETIC

<400> SEQUENCE: 233
tgcctttagt cagacgattg gcctgccaga attttttt                        37

<210> SEQ ID NO 234
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 234

```
gccacgctat acgtggtttg aagatatctt g                                           31

<210> SEQ ID NO 235
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 235
ggtggcgttg gtctccacag acaacgctca t                                           31

<210> SEQ ID NO 236
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 236
gcgcagagat atcaaatttg aagatatctt g                                           31

<210> SEQ ID NO 237
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 237
ggtggcgttg gtctcattat ttgacattat c                                           31

<210> SEQ ID NO 238
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 238
catatttaga aataccttg aagatatctt g                                            31

<210> SEQ ID NO 239
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 239
ggtggcgttg gtctcgaccg tgttaccttt t                                           31

<210> SEQ ID NO 240
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 240
ttttgtttaa gccttatttg aagatatctt g                                           31

<210> SEQ ID NO 241
<211> LENGTH: 31
<212> TYPE: DNA
```

```
<213> ORGANISM: ARTIFICIAL SEQUENCE
<220> FEATURE:
<223> OTHER INFORMATION: SYNTHETIC

<400> SEQUENCE: 241
ggtggcgttg gtctcaatca agaatcgaga a                                31

<210> SEQ ID NO 242
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 242
aatcaccaaa tagaaatttg aagatatctt g                                31

<210> SEQ ID NO 243
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 243
ggtggcgttg gtctcattca tatataacgg a                                31

<210> SEQ ID NO 244
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 244
cctcaagaat acatggtttg aagatatctt g                                31

<210> SEQ ID NO 245
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 245
ggtggcgttg gtctcctttt gatagaacca c                                31

<210> SEQ ID NO 246
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 246
agtttggagc ccttcagtgt gacaggtttg g                                31

<210> SEQ ID NO 247
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 247
ctgcactgat gttctccgcc tggttgcgct c                                31
```

<210> SEQ ID NO 248
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 248
cagctggcgg acgacggtgt gacaggtttg g             31

<210> SEQ ID NO 249
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 249
ctgcactgat gttctacagt atcgtagcca g             31

<210> SEQ ID NO 250
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 250
ggtagctagg ataaaagtgt gacaggtttg g             31

<210> SEQ ID NO 251
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 251
ctgcactgat gttctatttt tagttaacat c             31

<210> SEQ ID NO 252
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 252
tacctttaag gtctttgtgt gacaggtttg g             31

<210> SEQ ID NO 253
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 253
ctgcactgat gttctaccct gacaaagaag t             31

<210> SEQ ID NO 254
<211> LENGTH: 31
<212> TYPE: DNA
<213> ORGANISM: ARTIFICIAL SEQUENCE
<220> FEATURE:

-continued

<223> OTHER INFORMATION: SYNTHETIC

<400> SEQUENCE: 254
tttcaactat aggctggtgt gacaggtttg g                               31

<210> SEQ ID NO 255
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 255
ctgcactgat gttctgctga ccttgtatca t                               31

<210> SEQ ID NO 256
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 256
atatattctt ttttcagtgt gacaggtttg g                               31

<210> SEQ ID NO 257
<211> LENGTH: 31
<212> TYPE: DNA
<213> ORGANISM: ARTIFICIAL SEQUENCE
<220> FEATURE:
<223> OTHER INFORMATION: SYNTHETIC

<400> SEQUENCE: 257
ctgcactgat gttctcgttg aaaatagtta g                               31

<210> SEQ ID NO 258
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 258
acaaggagac cttgggtgga                                            20

<210> SEQ ID NO 259
<211> LENGTH: 200
<212> TYPE: DNA
<213> ORGANISM: ARTIFICIAL SEQUENCE
<220> FEATURE:
<223> OTHER INFORMATION: SYNTHETIC

<400> SEQUENCE: 259
caggtgcagt acaaggttct agtgttctag tgtattctgt tccgtctttc gttctagctt    60
gctgccttct tttgtcgata acgtatcgta cccgtttaat ggacacttcc tcatgagaca   120
gtatcagaga tcaatttagt cctcaaagag ttactcgtag ttgctacgct cgttccgatg   180
cgaggatctt ttaactggta                                              200

<210> SEQ ID NO 260
<211> LENGTH: 200
<212> TYPE: DNA
<213> ORGANISM: ARTIFICIAL SEQUENCE
<220> FEATURE:
<223> OTHER INFORMATION: SYNTHETIC

<400> SEQUENCE: 260
ctgctggcac agaagtatgt agtgttctag tgtattctgt tccgtctttc gttctagctt     60
gctgccttct tttgtcgata acgtatcgta cccgtttaat ggacacttcc tcatgagaca    120
gtatcagaga tcaatttagt cctcaaagag ttactcgtag ttgctacgct cgttccgatg    180
cgaggatctt ttaactggta                                                200

<210> SEQ ID NO 261
<211> LENGTH: 200
<212> TYPE: DNA
<213> ORGANISM: ARTIFICIAL SEQUENCE
<220> FEATURE:
<223> OTHER INFORMATION: SYNTHETIC

<400> SEQUENCE: 261
gctaagctgc tggcacagaa agtgttctag tgtattctgt tccgtctttc gttctagctt     60
gctgccttct tttgtcgata acgtatcgta cccgtttaat ggacacttcc tcatgagaca    120
gtatcagaga tcaatttagt cctcaaagag ttactcgtag ttgctacgct cgttccgatg    180
cgaggatctt ttaactggta                                                200

<210> SEQ ID NO 262
<211> LENGTH: 200
<212> TYPE: DNA
<213> ORGANISM: ARTIFICIAL SEQUENCE
<220> FEATURE:
<223> OTHER INFORMATION: SYNTHETIC

<400> SEQUENCE: 262
tcttagctgc tggcacagag agtgttctag tgtattctgt tccgtctttc gttctagctt     60
gctgccttct tttgtcgata acgtatcgta cccgtttaat ggacacttcc tcatgagaca    120
gtatcagaga tcaatttagt cctcaaagag ttactcgtag ttgctacgct cgttccgatg    180
cgaggatctt ttaactggta                                                200

<210> SEQ ID NO 263
<211> LENGTH: 200
<212> TYPE: DNA
<213> ORGANISM: ARTIFICIAL SEQUENCE
<220> FEATURE:
<223> OTHER INFORMATION: SYNTHETIC

<400> SEQUENCE: 263
tcttggctgc tggcacaaaa agtgttctag tgtattctgt tccgtctttc gttctagctt     60
gctgccttct tttgtcgata acgtatcgta cccgtttaat ggacacttcc tcatgagaca    120
gtatcagaga tcaatttagt cctcaaagag ttactcgtag ttgctacgct cgttccgatg    180
cgaggatctt ttaactggta                                                200

<210> SEQ ID NO 264
<211> LENGTH: 200
<212> TYPE: DNA
<213> ORGANISM: ARTIFICIAL SEQUENCE
<220> FEATURE:
<223> OTHER INFORMATION: SYNTHETIC

<400> SEQUENCE: 264
agagctggca cagaagtaca agtgttctag tgtattctgt tccgtctttc gttctagctt     60
gctgccttct tttgtcgata acgtatcgta cccgtttaat ggacacttcc tcatgagaca    120

```
gtatcagaga tcaatttagt cctcaaagag ttactcgtag ttgctacgct cgttccgatg    180
cgaggatctt ttaactggta                                                200
```

<210> SEQ ID NO 265
<211> LENGTH: 199
<212> TYPE: DNA
<213> ORGANISM: ARTIFICIAL SEQUENCE
<220> FEATURE:
<223> OTHER INFORMATION: SYNTHETIC

<400> SEQUENCE: 265

```
catcactgct ggcacagaaa gtgttctagt gtattctgtt ccgtctttcg ttctagcttg     60
ctgccttctt ttgtcgataa cgtatcgtac ccgtttaatg gacacttcct catgagacag    120
tatcagagat caatttagtc ctcaaagagt tactcgtagt tgctacgctc gttccgatgc    180
gaggatcttt taactggta                                                 199
```

<210> SEQ ID NO 266
<211> LENGTH: 200
<212> TYPE: DNA
<213> ORGANISM: ARTIFICIAL SEQUENCE
<220> FEATURE:
<223> OTHER INFORMATION: SYNTHETIC

<400> SEQUENCE: 266

```
agaaactgct ggcacagaga agtgttctag tgtattctgt tccgtctttc gttctagctt     60
gctgccttct tttgtcgata acgtatcgta cccgtttaat ggacacttcc tcatgagaca    120
gtatcagaga tcaatttagt cctcaaagag ttactcgtag ttgctacgct cgttccgatg    180
cgaggatctt ttaactggta                                                200
```

<210> SEQ ID NO 267
<211> LENGTH: 199
<212> TYPE: DNA
<213> ORGANISM: ARTIFICIAL SEQUENCE
<220> FEATURE:
<223> OTHER INFORMATION: SYNTHETIC

<400> SEQUENCE: 267

```
gctaaactgc tggcacacaa gtgttctagt gtattctgtt ccgtctttcg ttctagcttg     60
ctgccttctt ttgtcgataa cgtatcgtac ccgtttaatg gacacttcct catgagacag    120
tatcagagat caatttagtc ctcaaagagt tactcgtagt tgctacgctc gttccgatgc    180
gaggatcttt taactggta                                                 199
```

<210> SEQ ID NO 268
<211> LENGTH: 200
<212> TYPE: DNA
<213> ORGANISM: ARTIFICIAL SEQUENCE
<220> FEATURE:
<223> OTHER INFORMATION: SYNTHETIC

<400> SEQUENCE: 268

```
tctaagctgc ttgcacaaag agtgttctag tgtattctgt tccgtctttc gttctagctt     60
gctgccttct tttgtcgata acgtatcgta cccgtttaat ggacacttcc tcatgagaca    120
gtatcagaga tcaatttagt cctcaaagag ttactcgtag ttgctacgct cgttccgatg    180
cgaggatctt ttaactggta                                                200
```

<210> SEQ ID NO 269
<211> LENGTH: 200

```
<212> TYPE: DNA
<213> ORGANISM: ARTIFICIAL SEQUENCE
<220> FEATURE:
<223> OTHER INFORMATION: SYNTHETIC

<400> SEQUENCE: 269
tctctactgc tagcacagag agtgttctag tgtattctgt tccgtctttc gttctagctt      60
gctgccttct tttgtcgata acgtatcgta cccgtttaat ggacacttcc tcatgagaca     120
gtatcagaga tcaatttagt cctcaaagag ttactcgtag ttgctacgct cgttccgatg     180
cgaggatctt ttaactggta                                                 200

<210> SEQ ID NO 270
<211> LENGTH: 200
<212> TYPE: DNA
<213> ORGANISM: ARTIFICIAL SEQUENCE
<220> FEATURE:
<223> OTHER INFORMATION: SYNTHETIC

<400> SEQUENCE: 270
ctatactgct ggcacagaga agtgttctag tgtattctgt tccgtctttc gttctagctt      60
gctgccttct tttgtcgata acgtatcgta cccgtttaat ggacacttcc tcatgagaca     120
gtatcagaga tcaatttagt cctcaaagag ttactcgtag ttgctacgct cgttccgatg     180
cgaggatctt ttaactggta                                                 200

<210> SEQ ID NO 271
<211> LENGTH: 200
<212> TYPE: DNA
<213> ORGANISM: ARTIFICIAL SEQUENCE
<220> FEATURE:
<223> OTHER INFORMATION: SYNTHETIC

<400> SEQUENCE: 271
tccctagcac cacagagata agtgttctag tgtattctgt tccgtctttc gttctagctt      60
gctgccttct tttgtcgata acgtatcgta cccgtttaat ggacacttcc tcatgagaca     120
gtatcagaga tcaatttagt cctcaaagag ttactcgtag ttgctacgct cgttccgatg     180
cgaggatctt ttaactggta                                                 200

<210> SEQ ID NO 272
<211> LENGTH: 200
<212> TYPE: DNA
<213> ORGANISM: ARTIFICIAL SEQUENCE
<220> FEATURE:
<223> OTHER INFORMATION: SYNTHETIC

<400> SEQUENCE: 272
gattgactgc tggagcacaa agtgttctag tgtattctgt tccgtctttc gttctagctt      60
gctgccttct tttgtcgata acgtatcgta cccgtttaat ggacacttcc tcatgagaca     120
gtatcagaga tcaatttagt cctcaaagag ttactcgtag ttgctacgct cgttccgatg     180
cgaggatctt ttaactggta                                                 200

<210> SEQ ID NO 273
<211> LENGTH: 200
<212> TYPE: DNA
<213> ORGANISM: ARTIFICIAL SEQUENCE
<220> FEATURE:
<223> OTHER INFORMATION: SYNTHETIC

<400> SEQUENCE: 273
```

```
tacagactgc tggcacagag agtgttctag tgtattctgt tccgtctttc gttctagctt    60
gctgccttct tttgtcgata acgtatcgta cccgtttaat ggacacttcc tcatgagaca   120
gtatcagaga tcaatttagt cctcaaagag ttactcgtag ttgctacgct cgttccgatg   180
cgaggatctt ttaactggta                                              200
```

<210> SEQ ID NO 274
<211> LENGTH: 200
<212> TYPE: DNA
<213> ORGANISM: ARTIFICIAL SEQUENCE
<220> FEATURE:
<223> OTHER INFORMATION: SYNTHETIC

<400> SEQUENCE: 274

```
gacagactgc tggcacagag agtgttctag tgtattctgt tccgtctttc gttctagctt    60
gctgccttct tttgtcgata acgtatcgta cccgtttaat ggacacttcc tcatgagaca   120
gtatcagaga tcaatttagt cctcaaagag ttactcgtag ttgctacgct cgttccgatg   180
cgaggatctt ttaactggta                                              200
```

<210> SEQ ID NO 275
<211> LENGTH: 200
<212> TYPE: DNA
<213> ORGANISM: ARTIFICIAL SEQUENCE
<220> FEATURE:
<223> OTHER INFORMATION: SYNTHETIC

<400> SEQUENCE: 275

```
gcacagaagt acacagatgt agtgttctag tgtattctgt tccgtctttc gttctagctt    60
gctgccttct tttgtcgata acgtatcgta cccgtttaat ggacacttcc tcatgagaca   120
gtatcagaga tcaatttagt cctcaaagag ttactcgtag ttgctacgct cgttccgatg   180
cgaggatctt ttaactggta                                              200
```

<210> SEQ ID NO 276
<211> LENGTH: 200
<212> TYPE: DNA
<213> ORGANISM: ARTIFICIAL SEQUENCE
<220> FEATURE:
<223> OTHER INFORMATION: SYNTHETIC

<400> SEQUENCE: 276

```
tctctagaac tacagaaata agtgttctag tgtattctgt tccgtctttc gttctagctt    60
gctgccttct tttgtcgata acgtatcgta cccgtttaat ggacacttcc tcatgagaca   120
gtatcagaga tcaatttagt cctcaaagag ttactcgtag ttgctacgct cgttccgatg   180
cgaggatctt ttaactggta                                              200
```

<210> SEQ ID NO 277
<211> LENGTH: 200
<212> TYPE: DNA
<213> ORGANISM: ARTIFICIAL SEQUENCE
<220> FEATURE:
<223> OTHER INFORMATION: SYNTHETIC

<400> SEQUENCE: 277

```
agactccagg cacagaggta agtgttctag tgtattctgt tccgtctttc gttctagctt    60
gctgccttct tttgtcgata acgtatcgta cccgtttaat ggacacttcc tcatgagaca   120
gtatcagaga tcaatttagt cctcaaagag ttactcgtag ttgctacgct cgttccgatg   180
cgaggatctt ttaactggta                                              200
```

<210> SEQ ID NO 278
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 278
gtcacatttc tcagatcctc                          20

<210> SEQ ID NO 279
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 279
tacctctgtg ctgtgaggga                          20

<210> SEQ ID NO 280
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 280
ttactgcatt gtgactgaca                          20

<210> SEQ ID NO 281
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 281
gtacttctgc gcagtcagtg                          20

<210> SEQ ID NO 282
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 282
ctggaggact caggcactta                          20

<210> SEQ ID NO 283
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 283
cagcctggag actcagccat                          20

<210> SEQ ID NO 284
<211> LENGTH: 20
<212> TYPE: DNA
<213> ORGANISM: ARTIFICIAL SEQUENCE
<220> FEATURE:

<223> OTHER INFORMATION: SYNTHETIC

<400> SEQUENCE: 284
gactcggctg tgtactactg                                         20

<210> SEQ ID NO 285
<211> LENGTH: 18
<212> TYPE: DNA
<213> ORGANISM: ARTIFICIAL SEQUENCE
<220> FEATURE:
<223> OTHER INFORMATION: SYNTHETIC

<400> SEQUENCE: 285
gctctctacc tctgtgca                                           18

<210> SEQ ID NO 286
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 286
gctgtgtact tctgtgctac                                         20

<210> SEQ ID NO 287
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 287
ctcggctgtg tacttctgtg                                         20

<210> SEQ ID NO 288
<211> LENGTH: 19
<212> TYPE: DNA
<213> ORGANISM: ARTIFICIAL SEQUENCE
<220> FEATURE:
<223> OTHER INFORMATION: SYNTHETIC

<400> SEQUENCE: 288
catctacttc tgtgcagca                                          19

<210> SEQ ID NO 289
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 289
ctacatctgt gtggtgggcg                                         20

<210> SEQ ID NO 290
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 290
cagctgtcag actctgccct                                         20

```
<210> SEQ ID NO 291
<211> LENGTH: 18
<212> TYPE: DNA
<213> ORGANISM: ARTIFICIAL SEQUENCE
<220> FEATURE:
<223> OTHER INFORMATION: SYNTHETIC

<400> SEQUENCE: 291
acagactcag gcacttat                                                        18

<210> SEQ ID NO 292
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 292
tctcagcctg gagactcagc                                                      20

<210> SEQ ID NO 293
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 293
ttctgtgctc tctgggagct                                                      20

<210> SEQ ID NO 294
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 294
ttctgcgctc tctcggaact                                                      20

<210> SEQ ID NO 295
<211> LENGTH: 17
<212> TYPE: DNA
<213> ORGANISM: ARTIFICIAL SEQUENCE
<220> FEATURE:
<223> OTHER INFORMATION: SYNTHETIC

<400> SEQUENCE: 295
tatatttctg tgctatg                                                         17

<210> SEQ ID NO 296
<211> LENGTH: 20
<212> TYPE: DNA
<213> ORGANISM: ARTIFICIAL SEQUENCE
<220> FEATURE:
<223> OTHER INFORMATION: SYNTHETIC

<400> SEQUENCE: 296
caagtacttc tgtgcactgg                                                      20

<210> SEQ ID NO 297
<211> LENGTH: 20
<212> TYPE: DNA
<213> ORGANISM: ARTIFICIAL SEQUENCE
<220> FEATURE:
<223> OTHER INFORMATION: SYNTHETIC
```

```
<400> SEQUENCE: 297
tgtacctctg cgcagcaggt                                              20
```